US011213631B2

(12) United States Patent
Kim

(10) Patent No.: US 11,213,631 B2
(45) Date of Patent: Jan. 4, 2022

(54) PROTECTED NEEDLE ASSEMBLY FOR A HYPODERMIC NEEDLE

(71) Applicant: Difinity Solutions Inc., Nanaimo (CA)

(72) Inventor: David Sanghyuck Kim, Vancouver (CA)

(73) Assignee: Difinity Solutions Inc., Nanaimo (CA)

( * ) Notice: Subject to any disclaimer, the term of this patent is extended or adjusted under 35 U.S.C. 154(b) by 618 days.

(21) Appl. No.: 16/006,732

(22) Filed: Jun. 12, 2018

(65) Prior Publication Data

US 2018/0353711 A1    Dec. 13, 2018

Related U.S. Application Data

(60) Provisional application No. 62/518,689, filed on Jun. 13, 2017.

(51) Int. Cl.
*A61M 5/32* (2006.01)
*A61M 5/31* (2006.01)
*A61M 5/34* (2006.01)

(52) U.S. Cl.
CPC ........ *A61M 5/3245* (2013.01); *A61M 5/3137* (2013.01); *A61M 5/326* (2013.01); *A61M 5/3271* (2013.01); *A61M 5/347* (2013.01); *A61M 2005/3208* (2013.01); *A61M 2005/3247* (2013.01); *A61M 2005/3267* (2013.01); *A61M 2205/273* (2013.01)

(58) Field of Classification Search
CPC .. A61M 5/3245; A61M 5/3137; A61M 5/326; A61M 5/3271; A61M 5/347; A61M 2005/3208; A61M 2005/3247

USPC ........................................................ 604/198
See application file for complete search history.

(56) References Cited

U.S. PATENT DOCUMENTS

| 1,557,836 | A | 10/1925 | Hein |
| 2,922,419 | A | 1/1960 | Bednarz |
| 3,134,380 | A | 5/1964 | Armao |
| 3,378,008 | A | 4/1968 | Ogle |
| 3,580,251 | A | 5/1971 | Bourron-Marlotte |
| 3,659,587 | A | 5/1972 | Baldwin |

(Continued)

FOREIGN PATENT DOCUMENTS

| CA | 2049972 | 5/2000 |
| EP | 3122400 | 7/2019 |

(Continued)

OTHER PUBLICATIONS

Examiner's Report for corresponding Canadian Patent Application No. 3,007,875, dated Apr. 11, 2019.

(Continued)

*Primary Examiner* — Phillip A Gray
(74) *Attorney, Agent, or Firm* — Nicholas Garner; Oyen Wiggs Green & Mutala LLP

(57) ABSTRACT

There is provided a protected needle assembly. The assembly includes an outer barrel receiving a needle therethrough. The assembly includes an inner barrel resiliently biased to extend about the needle in a protected needle mode. The inner barrel is retractable into the outer barrel in a first instance to deploy the needle. The assembly includes a locking mechanism actuated upon the inner barrel moving towards the protected needle mode once more. The locking mechanism is configured to inhibit further retraction of the inner barrel thereafter.

20 Claims, 23 Drawing Sheets

(56) References Cited

U.S. PATENT DOCUMENTS

| | | |
|---|---|---|
| 3,659,602 A | 5/1972 | Cloyd |
| 3,850,174 A | 11/1974 | Ayres |
| 4,725,267 A | 2/1988 | Vaillancourt |
| 4,735,618 A | 4/1988 | Hagen |
| 4,747,829 A | 5/1988 | Jacob et al. |
| 4,767,413 A | 8/1988 | Haber et al. |
| 4,929,237 A | 5/1990 | Medway |
| 5,114,404 A | 5/1992 | Paxton et al. |
| 5,135,510 A | 8/1992 | Maszkiewicz et al. |
| 5,147,323 A | 9/1992 | Haber et al. |
| 5,195,983 A | 3/1993 | Boese |
| 5,222,945 A | 6/1993 | Basnight |
| 5,269,761 A | 12/1993 | Stehrenberger et al. |
| 5,279,586 A | 1/1994 | Balkwill |
| 5,354,284 A | 10/1994 | Haber et al. |
| 5,425,715 A | 6/1995 | Dalling et al. |
| 5,472,430 A | 12/1995 | Vaillancourt et al. |
| 5,637,094 A | 6/1997 | Stewart, Jr. et al. |
| 5,695,472 A | 12/1997 | Wyrick |
| 5,893,845 A | 4/1999 | Newby et al. |
| 5,980,494 A | 11/1999 | Malencheck et al. |
| 6,416,497 B1 | 7/2002 | Kirk |
| 6,676,641 B2 | 1/2004 | Woodward, Jr. |
| 6,855,129 B2 * | 2/2005 | Jensen .................. A61M 5/326 604/110 |
| 6,926,697 B2 | 8/2005 | Malencheck |
| 7,648,483 B2 | 1/2010 | Edwards et al. |
| 7,717,877 B2 | 5/2010 | Lavi et al. |
| 7,799,002 B2 | 9/2010 | Dillard, III |
| 9,028,453 B2 | 5/2015 | Jennings |
| 9,440,026 B2 | 9/2016 | Wozencroft |
| 2002/0010432 A1 | 1/2002 | Klitmose |
| 2005/0283120 A1 | 12/2005 | Wang |
| 2010/0137808 A1 | 6/2010 | Wilmot et al. |
| 2015/0011943 A1 | 1/2015 | Holmes et al. |
| 2018/0126083 A1 | 5/2018 | Schmid et al. |

FOREIGN PATENT DOCUMENTS

| | | |
|---|---|---|
| WO | PCTUS9002930 | 12/1991 |
| WO | PCTUS9200354 | 7/1993 |
| WO | PCTUS9307819 | 3/1994 |
| WO | 95/29721 | 11/1995 |
| WO | WO2013065055 | 5/2013 |
| WO | WO2016210404 | 12/2016 |

OTHER PUBLICATIONS

International Search Report issued on PCT/CA2020/051157 dated Oct. 15, 2020.

* cited by examiner

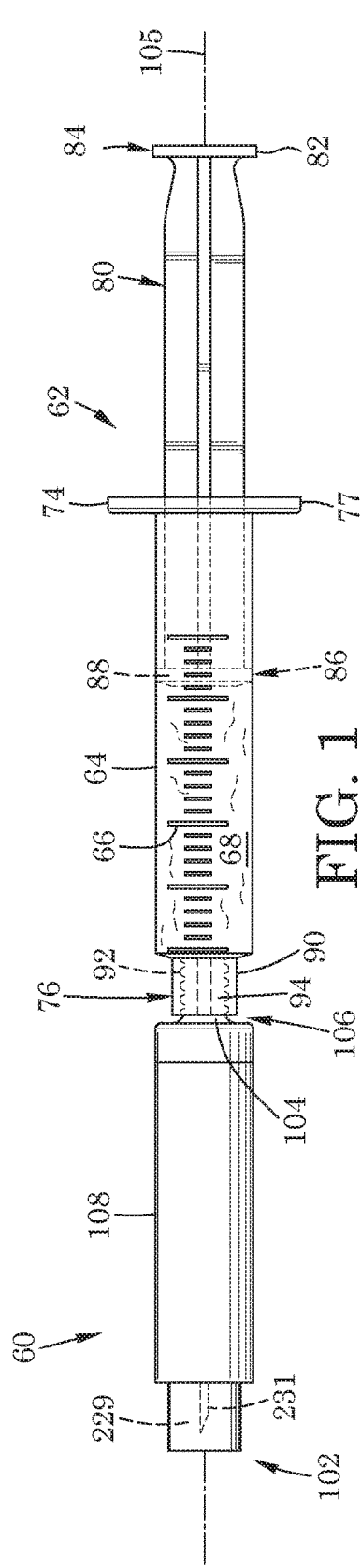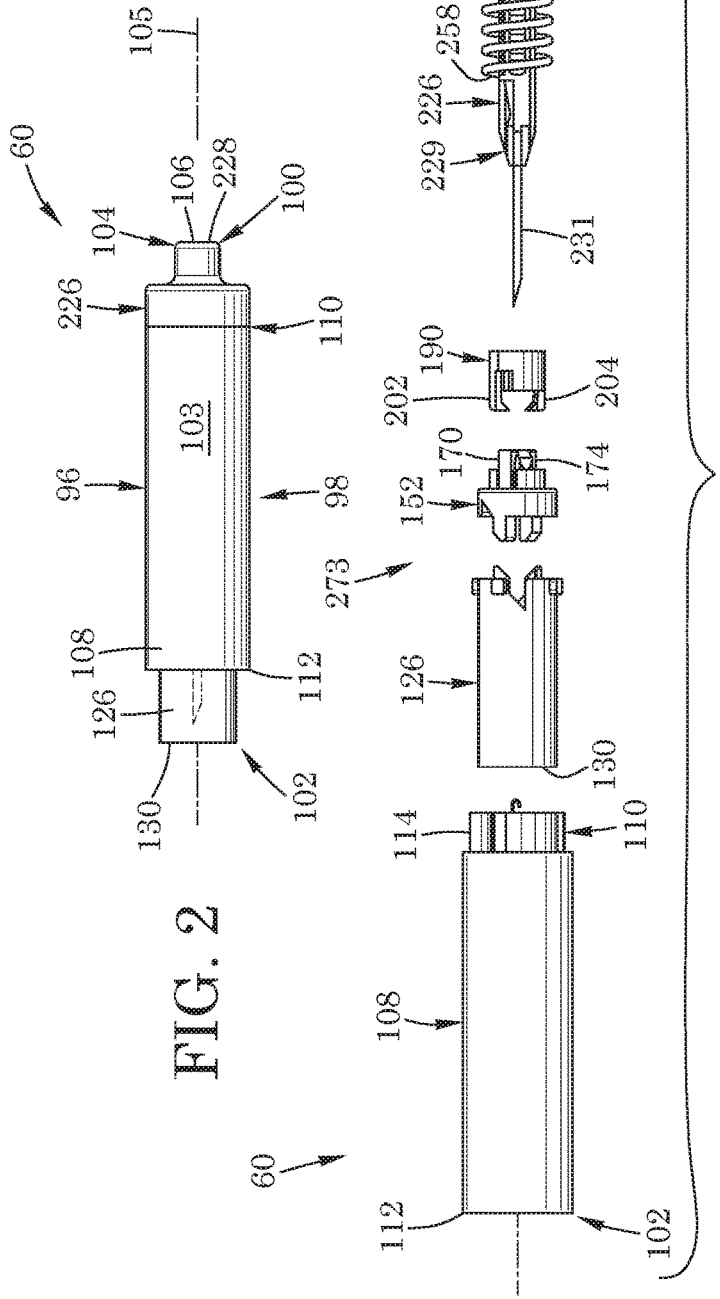

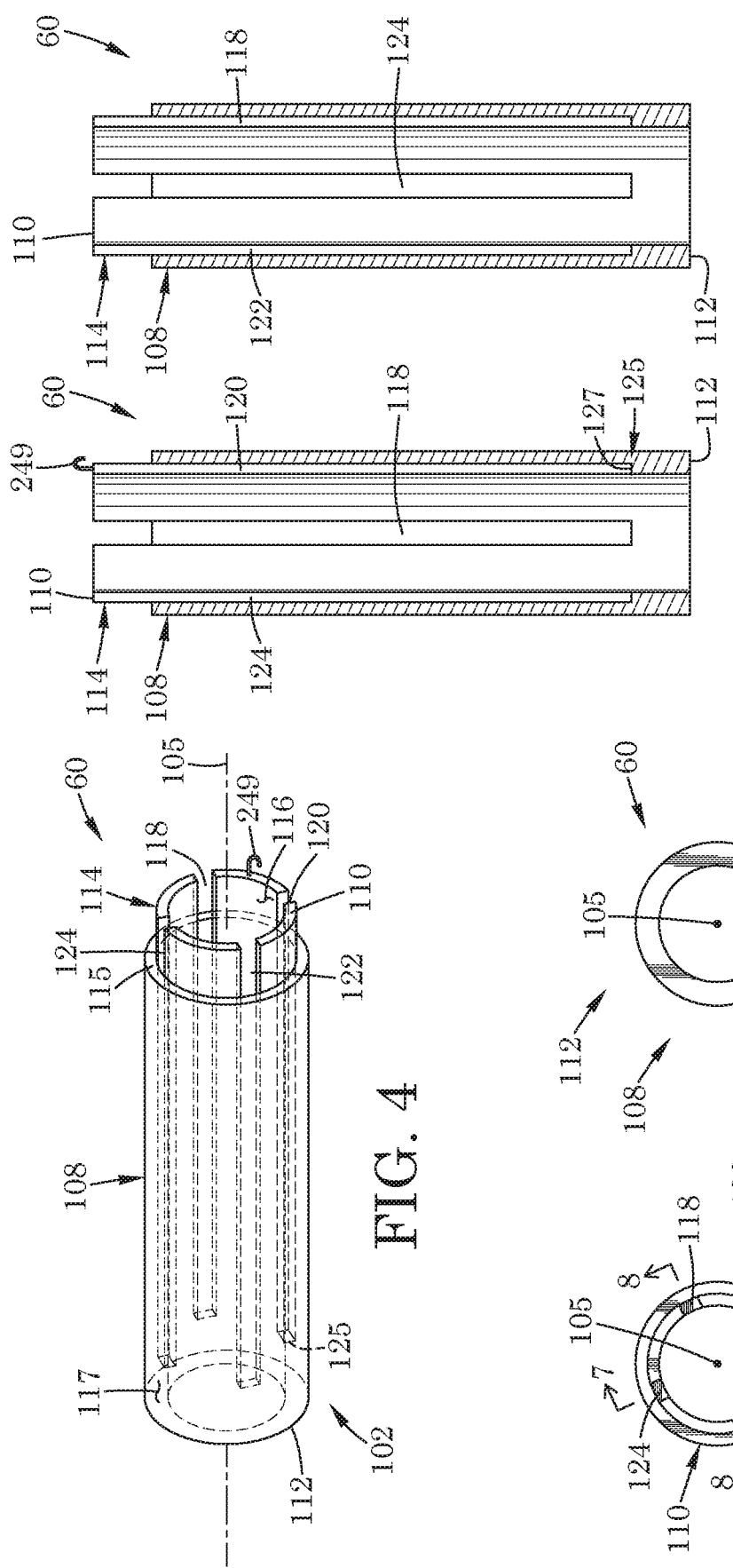

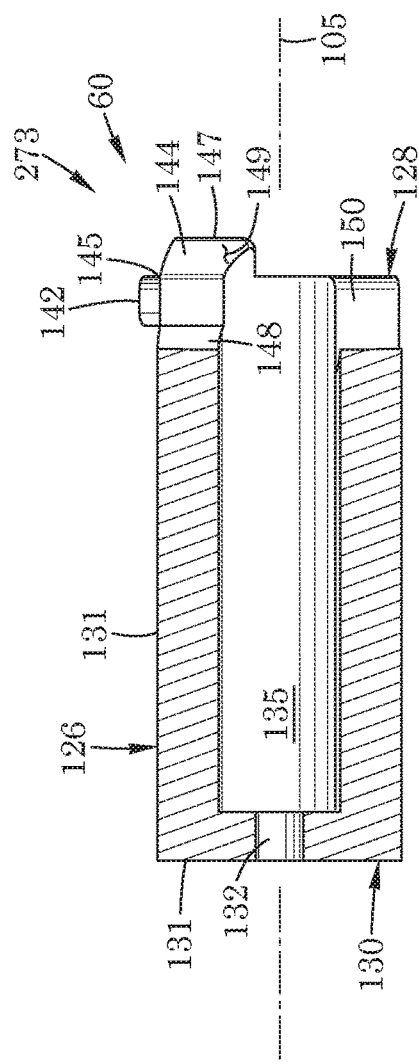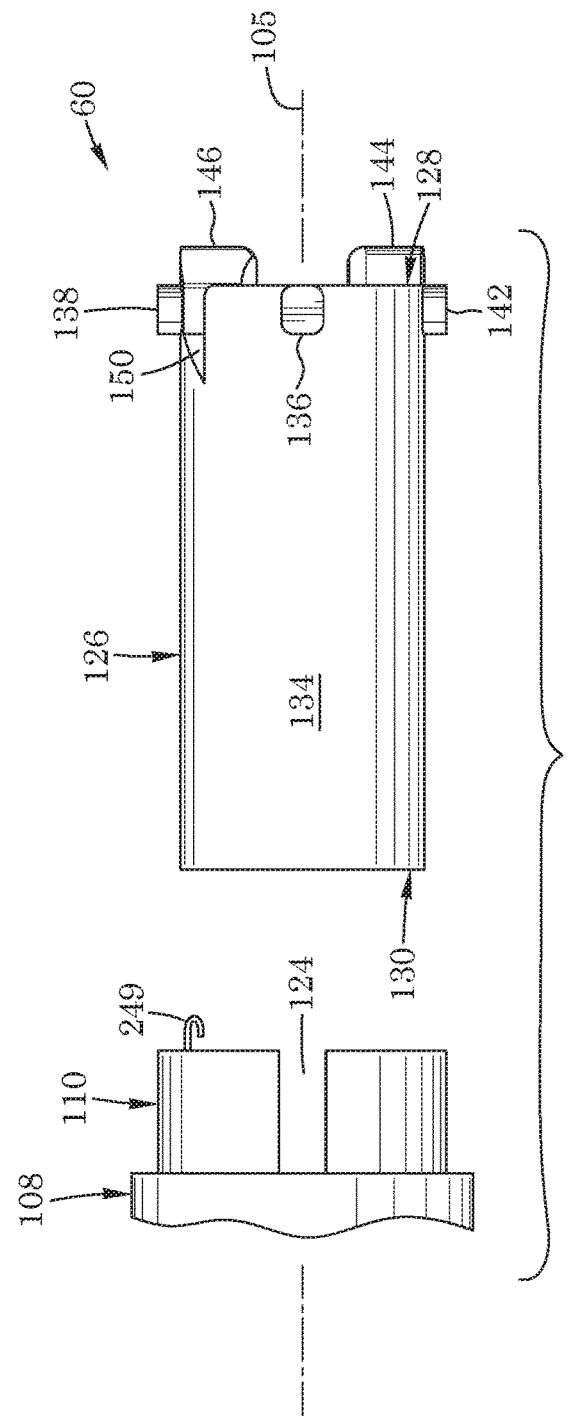

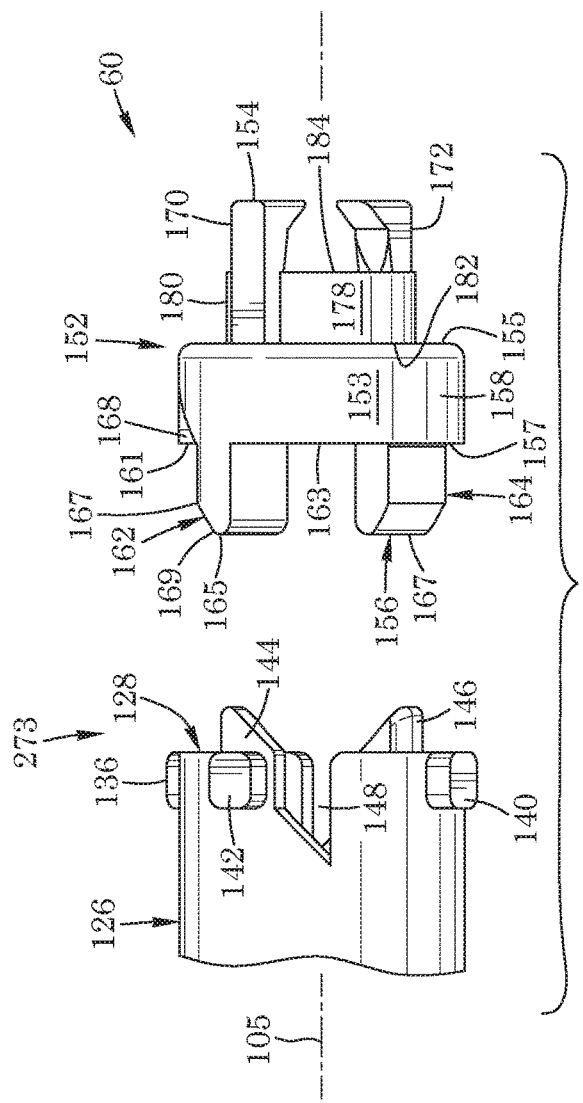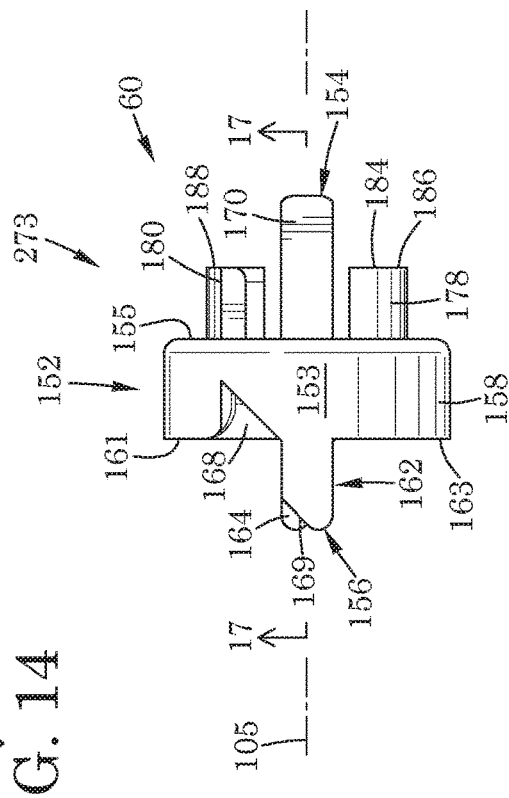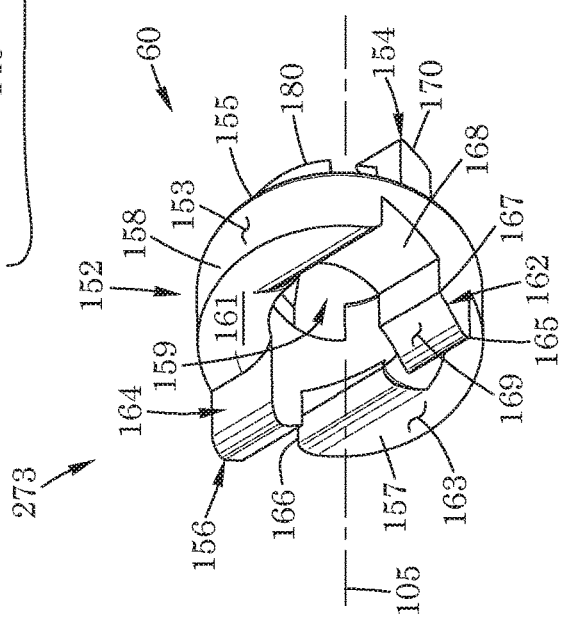
FIG. 14
FIG. 16
FIG. 15

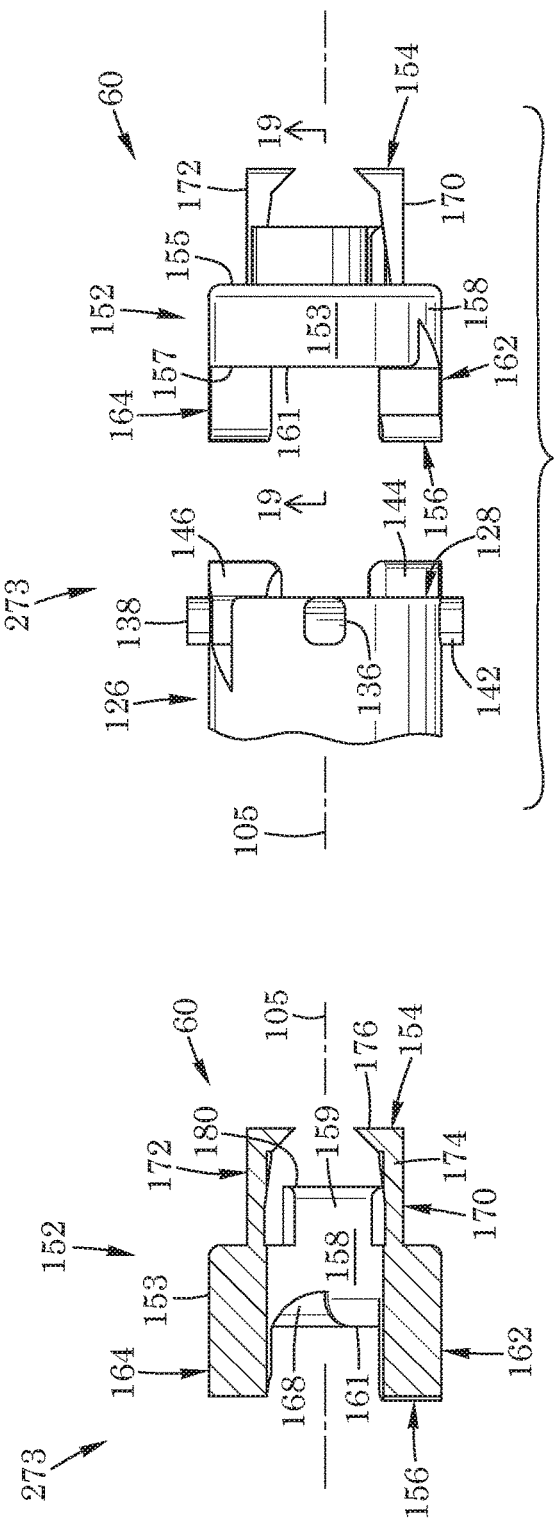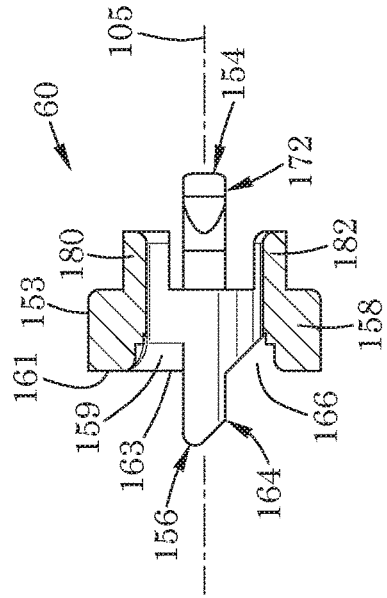
FIG. 17
FIG. 18
FIG. 19

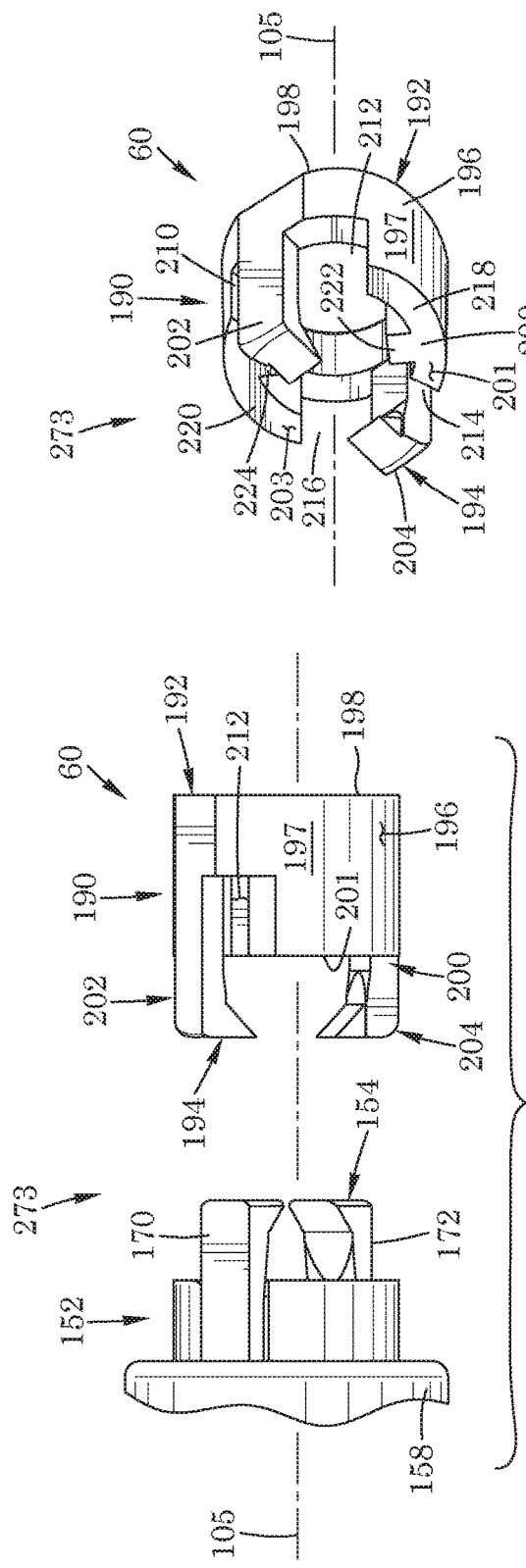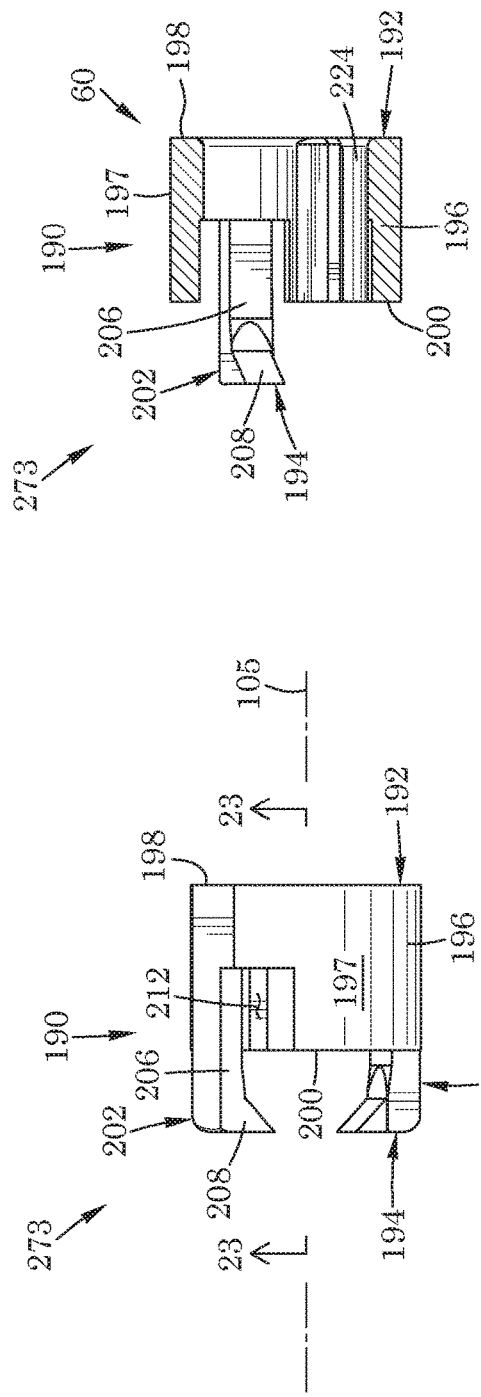

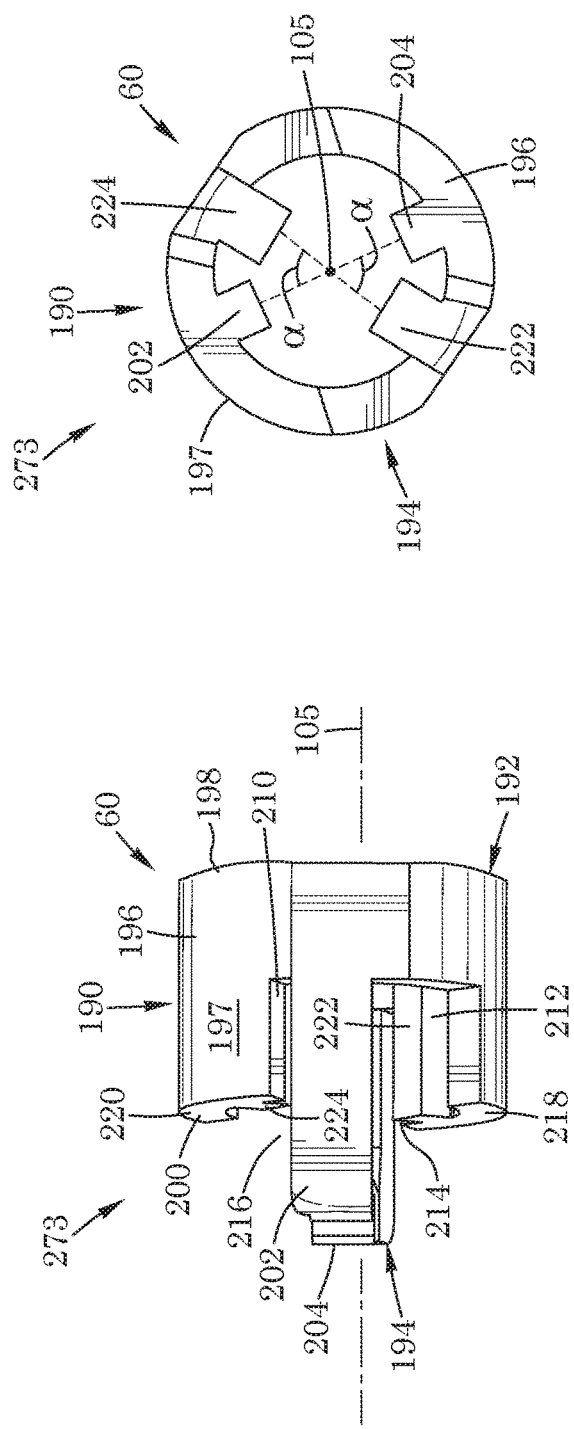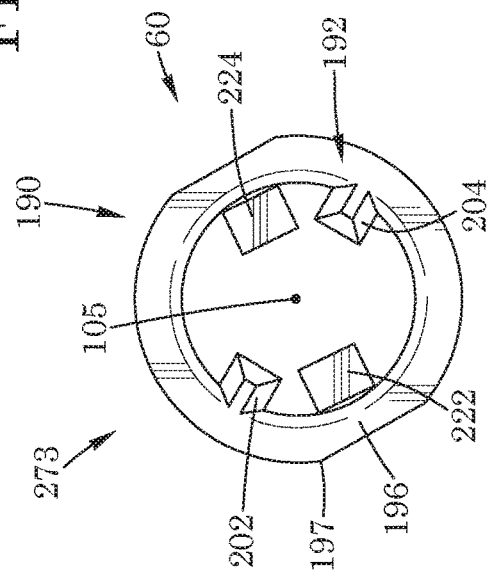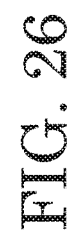

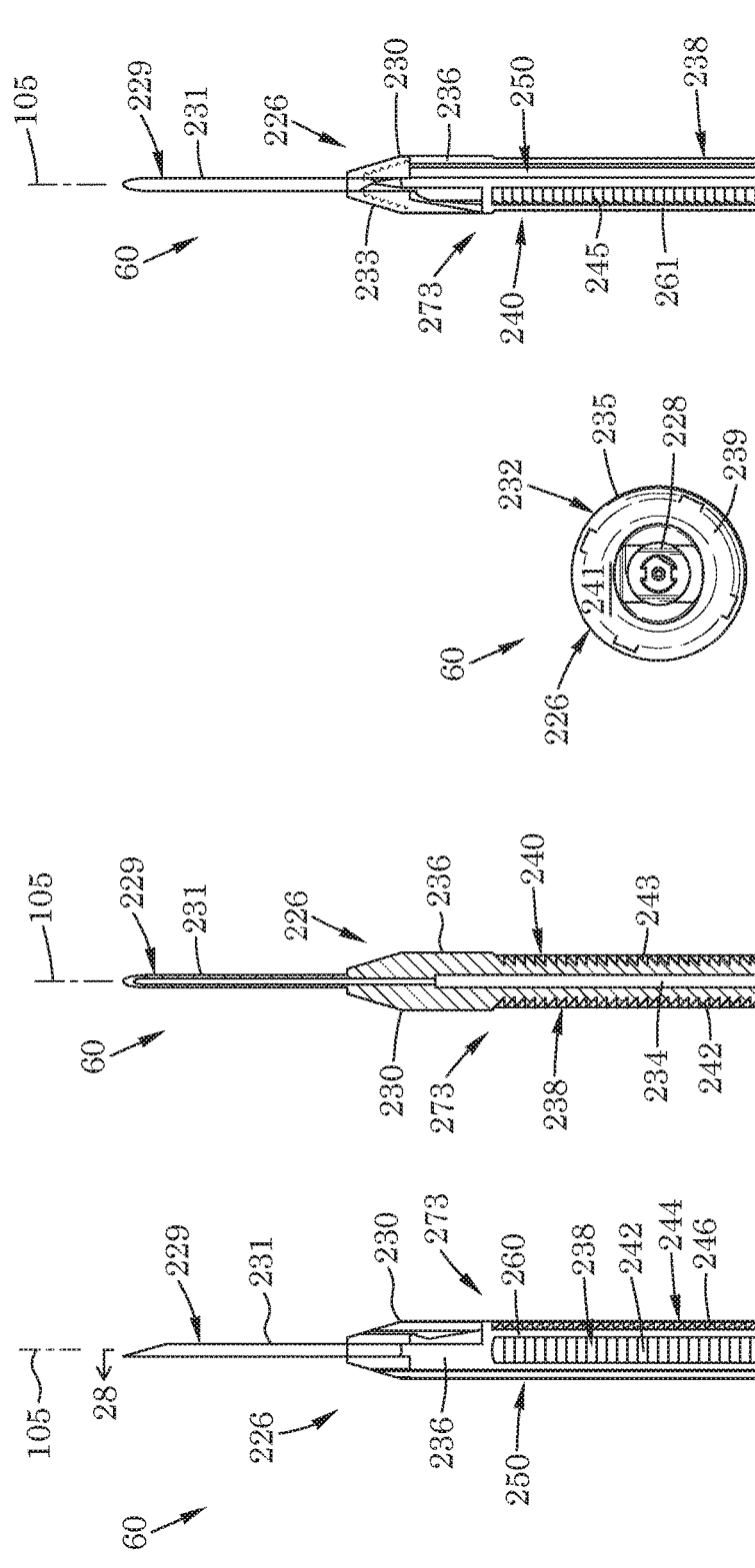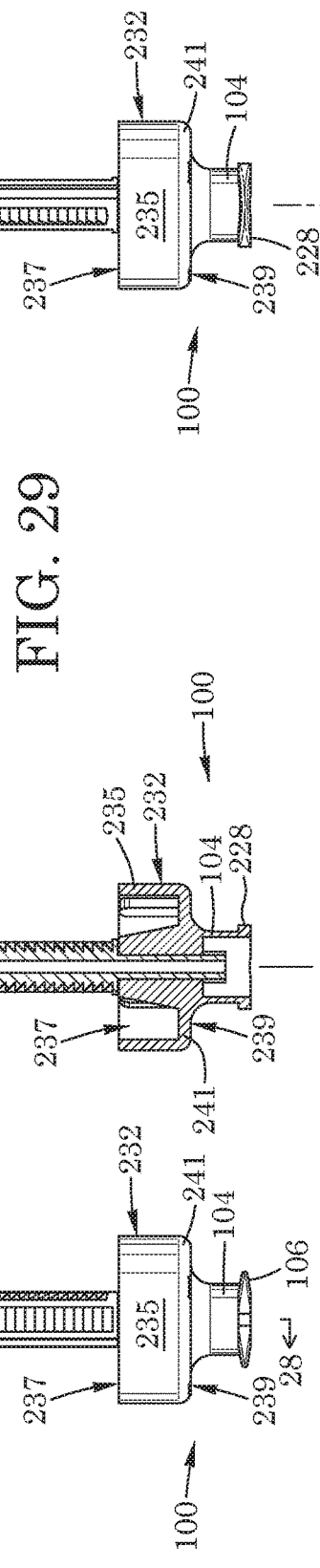

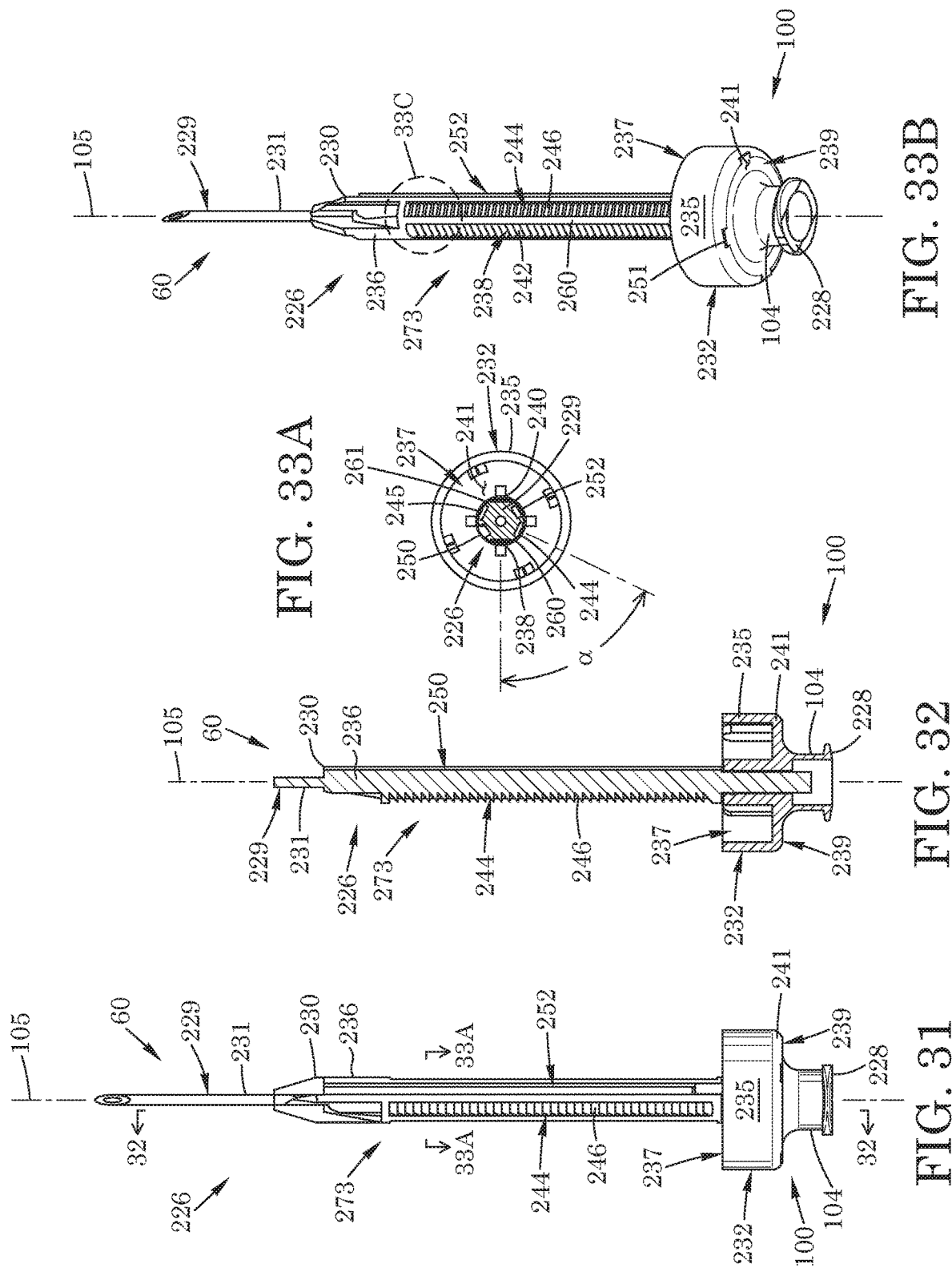

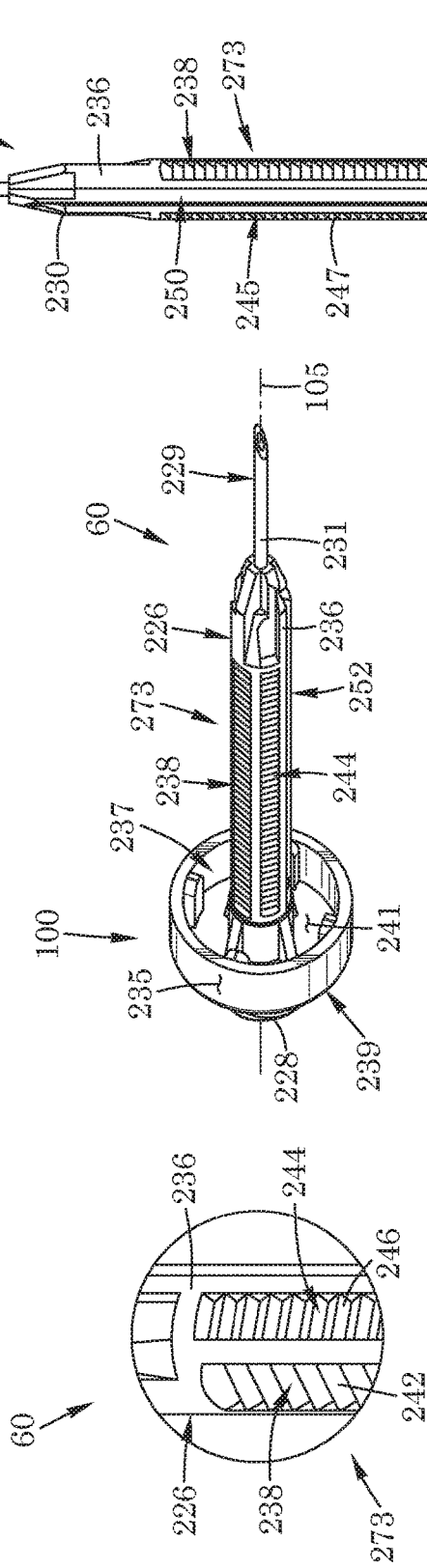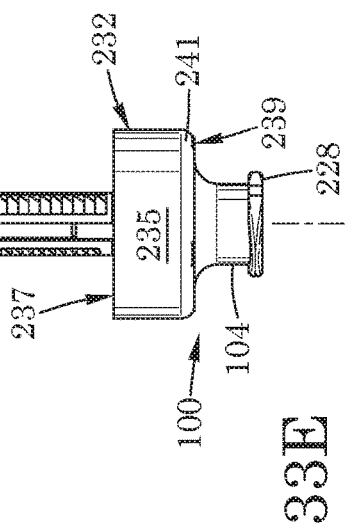
FIG. 33C
FIG. 33D
FIG. 33E

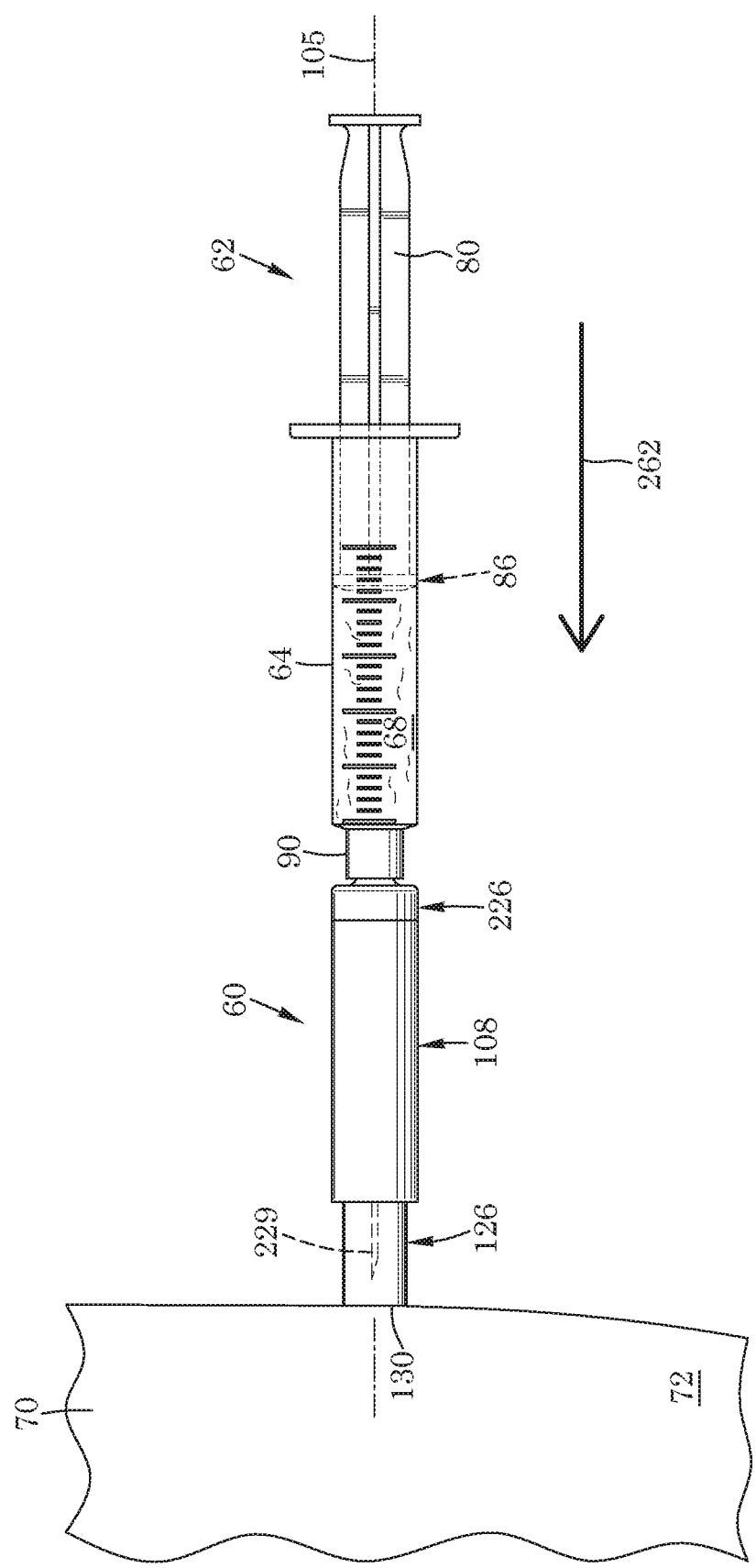

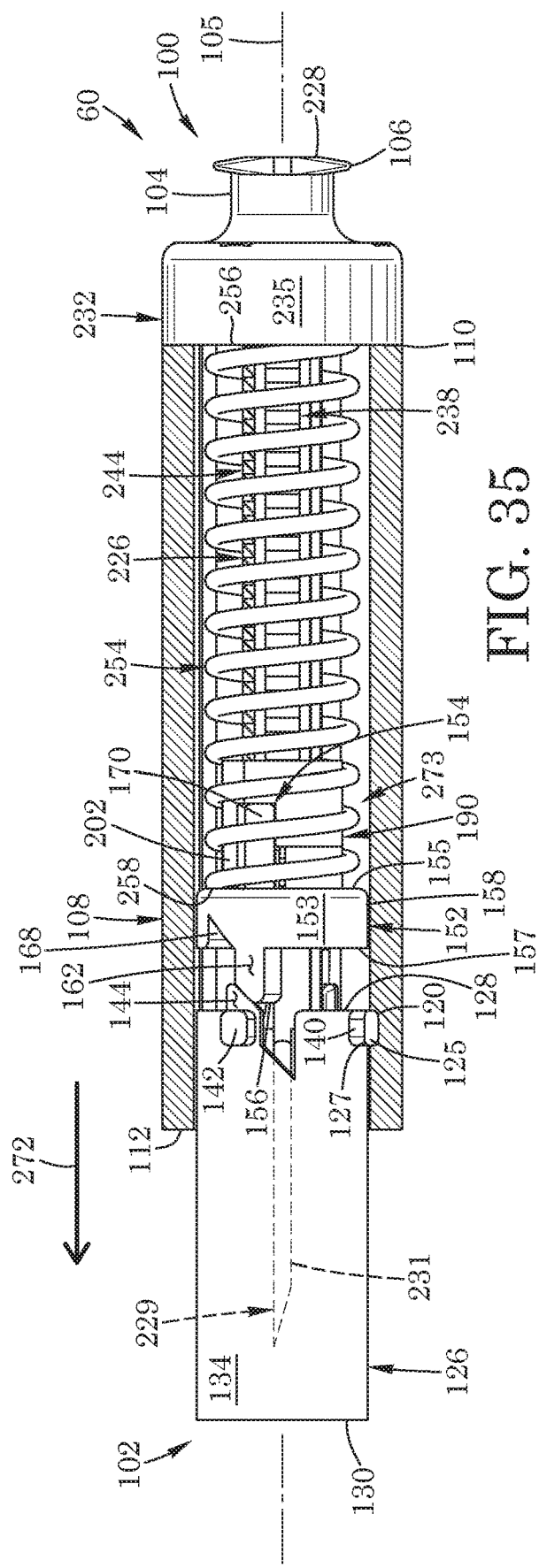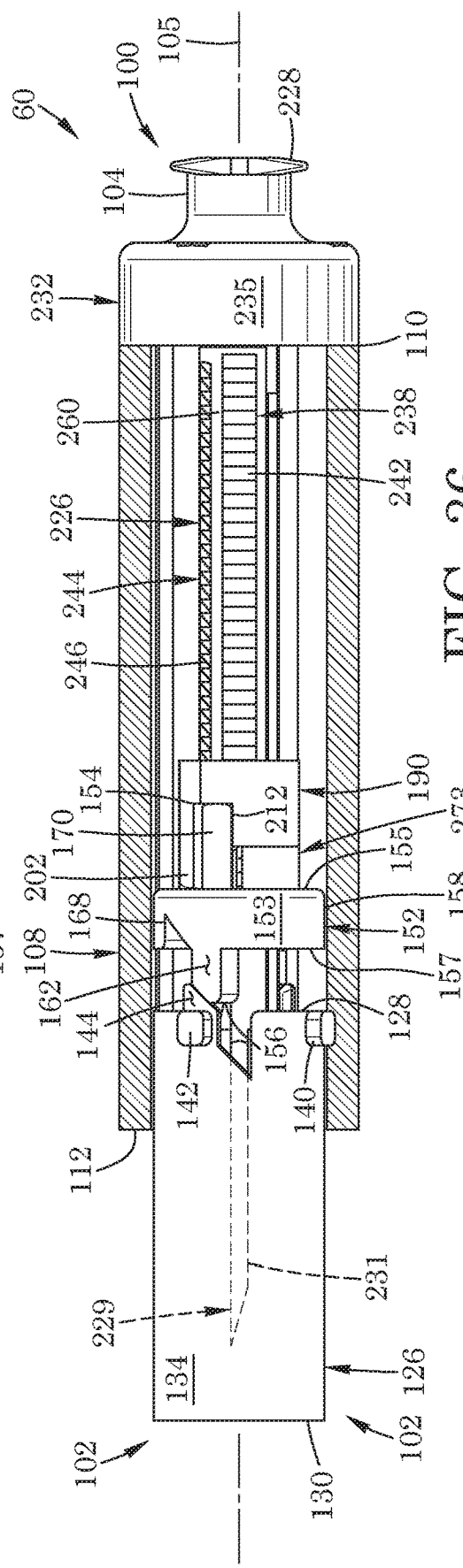

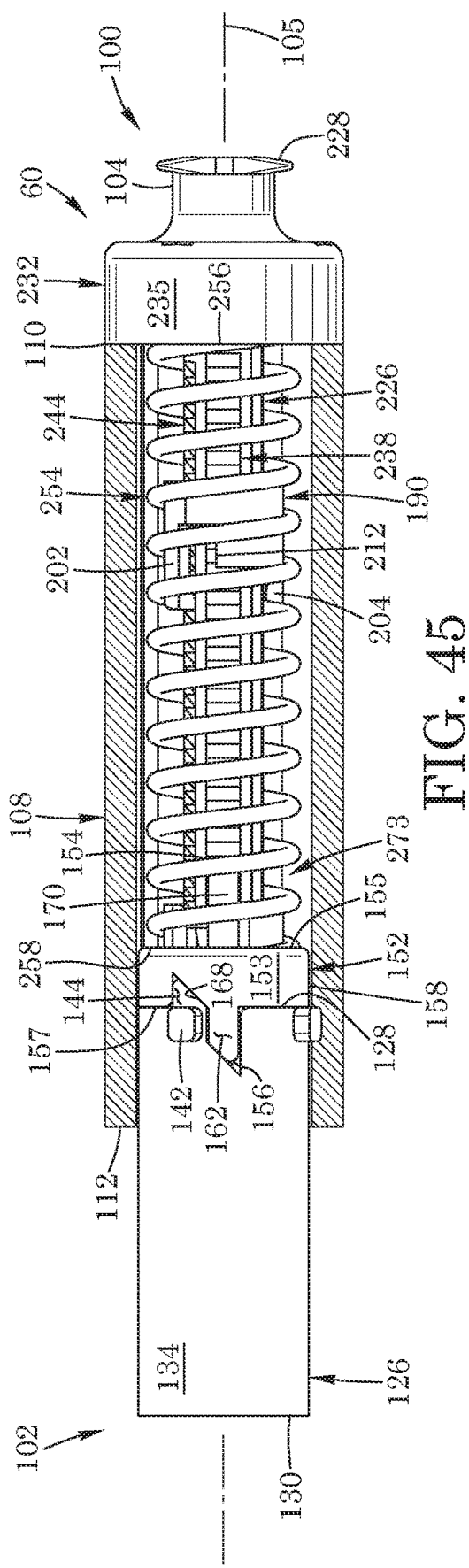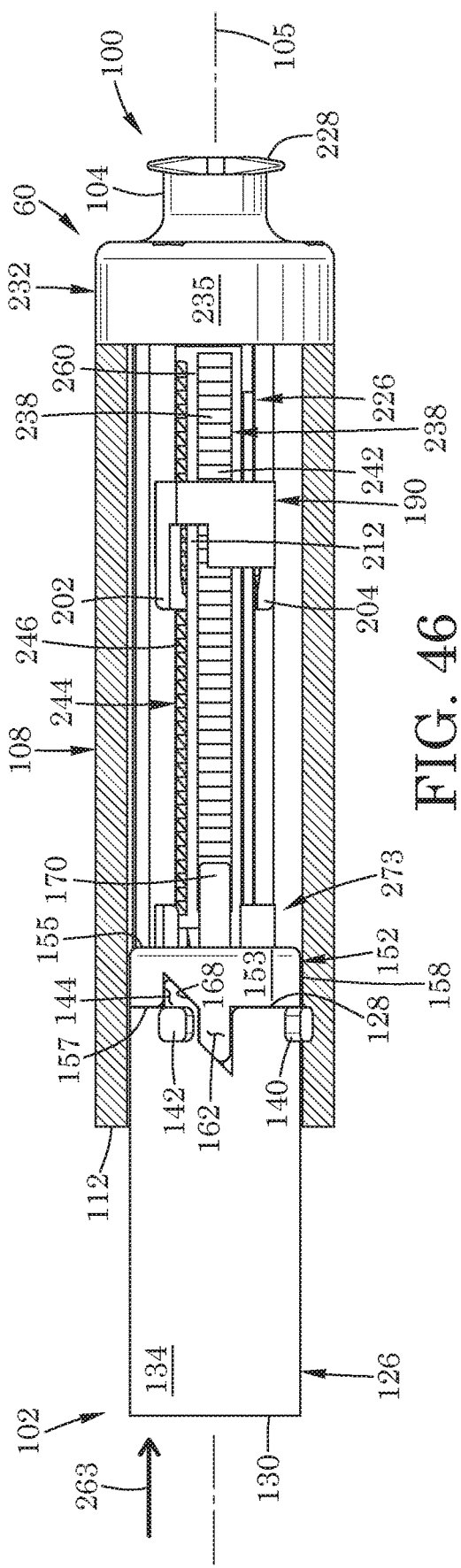

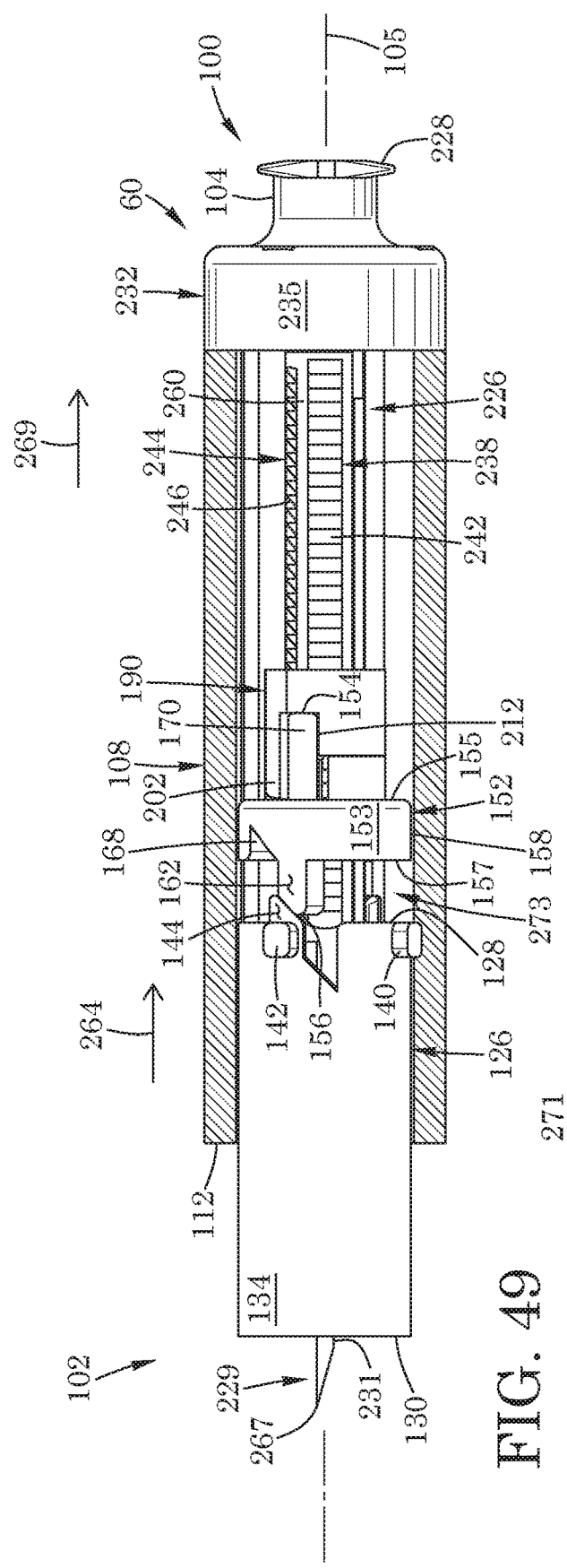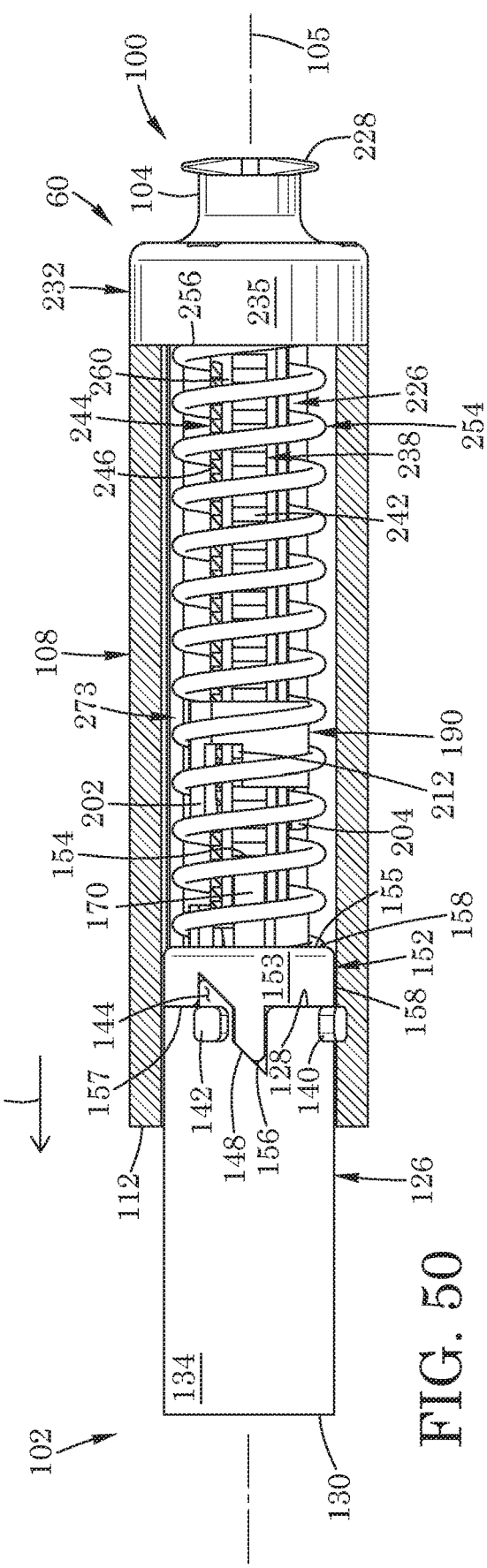

PROTECTED NEEDLE ASSEMBLY FOR A HYPODERMIC NEEDLE

FIELD OF THE INVENTION

There is provided a protected needle assembly. In particular, there is provided a protected needle assembly for a hypodermic needle.

DESCRIPTION OF THE RELATED ART

U.S. Pat. No. 4,929,237 to Medway discloses a safety device for preventing contact with exposed contaminated hypodermic needles. The safety device includes a housing unit, syringe, hypodermic needle and spring for retracting the hypodermic needle. The safety device includes safety elements to prevent accidental removal of the syringe from the housing unit and exposure of the needle.

U.S. Pat. No. 6,926,697 to Malenchek discloses a safety syringe which includes a shield and a barrel mounted for reciprocating movement within the shield. The safety syringe includes a hub sized and shaped so as to be attached to the barrel and a ring rotatably mounted to the hub. The ring includes a tab that cooperates with the grooves in the interior wall of the shield for locking the barrel within the shield so as to allow for a single use of the safety syringe.

U.S. Pat. No. 5,135,510 to Maszkiewicz discloses a device for preventing exposure of a contaminated hypodermic needle to health care personnel. A syringe barrel having a flange at one end and a hypodermic needle at the other end is adapted to receive a plunger. A protective guard fits around the syringe barrel and moves relative thereto. The protective guard can assume different positions in which the hypodermic needle is either exposed or retracted in the protective guard. The protective guard is spring biased to a guarded position which covers the hypodermic needle. A ratcheting mechanism provided on the protective guard and the syringe barrel restricts that movement of the protective guard which exposes the hypodermic needle. When the needle has been used and is being removed from the patient's body, the syringe barrel and hypodermic needle retract inside the protective guard and the ratcheting mechanism may be disabled to permanently secure the needle in the guarded position.

BRIEF SUMMARY OF INVENTION

The present invention provides, and it is an object to provide, an improved protected needle assembly for a hypodermic needle.

According to a first aspect, there is accordingly provided a protected needle assembly. The assembly includes an outer barrel receiving a needle therethrough. The assembly includes an inner barrel resiliently biased to extend about the needle in a protected needle mode. The inner barrel is retractable into the outer barrel in a first instance to deploy the needle. The assembly includes a locking mechanism actuated upon the inner barrel moving towards the protected needle mode once more. The locking mechanism is configured to inhibit further retraction of the inner barrel thereafter.

According to a second aspect, there is provided a protected needle assembly. The assembly includes an outer barrel receiving a needle therethrough. The assembly includes an inner barrel resiliently biased to extend about the needle in a protected needle mode. The assembly includes a catch and serrated channel system configured to enable the inner barrel to at least partially retract into the outer barrel to deploy the needle for a one-time use, with subsequent retraction of the inner barrel being inhibited.

According to a third aspect, there is provided a protected needle assembly. The assembly includes an outer barrel having a first end operatively connectable with a syringe and an open second end shaped to receive a hypodermic needle therethrough. The assembly includes an inner barrel slidably engageable with and outwardly biased from the outer barrel so as to extend about the needle. The assembly includes a hub disposed within the outer barrel and outwardly biased to engage with the inner barrel. The assembly includes an annular latch member disposed within the outer barrel and engageable with the hub to inhibit rotation thereof, whereby during an injection the inner barrel, the hub and the latch member retract towards the first end of the outer barrel, and thereafter the latch member is configured to remain in place while the hub and the inner barrel bias outwards once more, with the hub disengaging from the latch member and rotating into a position that enables movement of the inner barrel and the hub towards the second end of the outer barrel and inhibits any further retraction of said inner barrel.

According to a fourth aspect, there is provided a protected needle assembly. The assembly includes an outer barrel having a first end operatively connectable with a syringe and an open second end shaped to receive a hypodermic needle therethrough. The assembly includes a centrally-positioned elongate member about which the outer barrel extends. The elongate member has a first end coupled to the first end of the outer barrel. The elongate member is co-axial with the outer barrel. The elongate member has a second end to which the hypodermic needle is connectable. The elongate member includes a smooth surface, a first serrated channel and a second serrated channel. The smooth surface and the channels are outwardly-facing, longitudinally-extending and circumferentially spaced-apart from each other. The assembly includes an inner barrel slidably engageable with and outwardly biased towards the second end of the outer barrel so as to extend about the needle. The inner barrel includes a guide member that is angled at least in part. The assembly includes an annular latch member. The latch member includes a catch engageable with the first serrated channel. The first serrated channel is configured to enable movement of the latch member towards the first end of the outer barrel and to inhibit movement of the latch member towards the second end of the outer barrel. The latch member includes a rotation-locking recess. The assembly includes a hub outwardly biased to abut the guide member of the inner barrel. The hub includes a catch slidably engageable with the elongate member via said smooth surface. At least a portion of the catch of the hub is shaped to extend within the rotation-locking recess of the latch member. The rotation-locking recess of the latch member inhibits angular rotation of the hub thereby. When the inner barrel abuts a patient's body, the inner barrel, the hub and the latch member selectively retract towards the first end of the outer barrel to enable the needle to enter into the body. The latch member is held in place via the catch thereof thereafter while the hub and the inner barrel are resiliently biased towards the second end until the catch of the hub dislodges from the rotation-locking recess of the latch member, at which point the guide member of the inner barrel promotes angular rotation of the catch of the hub from said smooth surface to the second serrated channel, which functions to inhibit retraction of the inner barrel towards the first end of the outer barrel thereafter.

BRIEF DESCRIPTION OF DRAWINGS

The invention will be more readily understood from the following description of preferred embodiments thereof given, by way of example only, with reference to the accompanying drawings, in which:

FIG. 1 is a side elevation view of a protected needle assembly having a proximal end and a distal end, a hypodermic needle shown partially in ghost coupled to the assembly adjacent to the distal end thereof, and a syringe coupled to the proximal end of the assembly, the syringe including a graduated barrel and a plunger engageable with the graduated barrel, the plunger being shown in an extended position;

FIG. 2 is a side elevation view of the protected needle assembly of FIG. 1 and the hypodermic needle of FIG. 1 partially shown in ghost;

FIG. 3 is an exploded, side perspective view of the protected needle assembly and the hypodermic needle of FIG. 1, the assembly including an outer barrel, an inner barrel slidably engageable with the outer barrel, an elongate member shaped to couple with the outer barrel and the hypodermic needle, a hub engageable with the inner barrel and the elongate member, an annular latch member engaged with the hub and the elongate member, and a spring engaged with the hub and the elongate member;

FIG. 4 is a side, proximal end perspective view of the outer barrel of FIG. 3, the outer barrel including a plurality of circumferentially spaced-apart channels extending longitudinally within the interior thereof, with the channels being shown partially in ghost;

FIG. 5 is a proximal end elevation view of the outer barrel of FIG. 4;

FIG. 6 is a distal end elevation view of the outer barrel of FIG. 4;

FIG. 7 is a sectional view taken along lines 7-7 of the outer barrel of FIG. 5;

FIG. 8 is a sectional view taken along lines 8-8 of the outer barrel of FIG. 5;

FIG. 12 is a sectional view taken along lines 12-12 of the inner barrel of FIG. 9;

FIG. 13 is an exploded, top perspective view of the outer barrel and the inner barrel of FIG. 9, with the outer barrel being shown in fragment;

FIG. 14 is an exploded, side perspective view of the inner barrel and the hub of FIG. 3, with the inner barrel being shown in fragment;

FIG. 15 is a distal end, side, top perspective view of the hub of FIG. 14;

FIG. 16 is a side elevation view of the hub of FIG. 14;

FIG. 17 is a sectional view taken along lines 17-17 of the hub of FIG. 16;

FIG. 18 is an exploded, top perspective view of the inner barrel and the hub of FIG. 3, with the inner barrel being shown in fragment;

FIG. 19 is a sectional view taken along lines 19-19 of the hub of FIG. 18;

FIG. 20 is an exploded, side perspective view of the hub and the latch member of FIG. 3, with the hub being shown in fragment;

FIG. 21 is a distal end, top, side perspective view of the latch member of FIG. 20;

FIG. 22 is a side elevation view of the latch member of FIG. 20;

FIG. 23 is a sectional view taken along lines 23-23 of the latch member of FIG. 22;

FIG. 24 is a top perspective view of the latch member of FIG. 20;

FIG. 25 is a distal end elevation view of the latch member of FIG. 24;

FIG. 26 is a proximal end elevation view of the latch member of FIG. 24;

FIG. 27 is a front elevation view of the elongate member and hypodermic needle of FIG. 3;

FIG. 28 is a sectional view taken along lines 28-28 of the elongate member and hypodermic needle of FIG. 27;

FIG. 29 is a proximal end view of the elongate member of FIG. 27;

FIG. 30 is a left side elevation view of the elongate member and hypodermic needle of FIG. 27;

FIG. 31 is a right side elevation view of the elongate member and hypodermic needle of FIG. 27;

FIG. 32 is a sectional view taken along lines 32-32 of the elongate member and hypodermic needle of FIG. 31;

FIG. 33A is a sectional view taken along lines 33-33 of the elongate member of FIG. 31;

FIG. 33B is a proximal end, front, right side perspective view of the elongate member and hypodermic needle of FIG. 27;

FIG. 33C is an enlarged, fragmentary perspective view of a shaft portion of the elongate member of FIG. 33B;

FIG. 33D is a distal end, front, right side perspective view of the elongate member and hypodermic needle of FIG. 27;

FIG. 33E is a front, left side perspective view of the elongate member and hypodermic needle of FIG. 27;

FIG. 34 is a side elevation view of the syringe, the protected needle assembly and the hypodermic needle of FIG. 1 in a pre-injection mode, with the hypodermic needle being partially shown in ghost, with the plunger being in its extended position, with the inner barrel of the assembly fully extending outwards from the outer barrel so as to extend about the hypodermic needle, and with the inner barrel abutting the arm of a patient, the patient being shown in fragment;

FIG. 35 is a side elevation view of the assembly and hypodermic needle of FIG. 34, with the hypodermic needle being shown partially in ghost, with a right side half of the outer barrel of the assembly being removed to reveal positioning of the inner barrel, hub, latch member and spring in the pre-injection mode, with the hub abutting guide members of the inner barrel and being shown in an injection angular position;

FIG. 36 is a side elevation view of the assembly and hypodermic needle of FIG. 34, with the hypodermic needle being shown partially in ghost, with the right side half of the outer barrel and the spring of the assembly being removed to reveal positioning of the inner barrel, hub and latch member in the pre-injection mode;

FIG. 45 is a side elevation view of the assembly and hypodermic needle of FIG. 44, with the hypodermic needle being shown partially in ghost, with the right side half of the outer barrel of the assembly being removed to reveal positioning of the inner barrel, hub, latch member and spring in the post-injection mode, and with the inner barrel of the assembly fully extending outwards from the outer barrel of the assembly so as to extend about the hypodermic needle so fully removed;

FIG. 46 is a side elevation view of the assembly and hypodermic needle of FIG. 44, with the hypodermic needle being shown partially in ghost, with the right side half of the outer barrel and the spring of the assembly being removed to reveal positioning of the inner barrel, hub, latch member and spring in the post-injection mode, and with the inner barrel of the assembly fully extending outwards from the outer barrel of the assembly so as to extend about the hypodermic needle so fully removed;

FIG. 49 is a side elevation view of the assembly and hypodermic needle of FIG. 48, with the right side half of the outer barrel and the spring of the assembly being removed to reveal positioning of the inner barrel, hub and latch member in the needle-insertion mode according to said second aspect; and FIG. 50 is a side elevation view of the assembly and hypodermic needle of FIG. 49, with the hypodermic needle being shown partially in ghost, with the right side half of the outer barrel of the assembly being removed to reveal positioning of the inner barrel, hub, latch member and spring in the post-injection mode, and with the inner barrel of the assembly fully extending outwards from the outer barrel of the assembly so as to extend about the hypodermic needle so fully removed;

DESCRIPTION OF THE PREFERRED EMBODIMENTS

Figure 9:
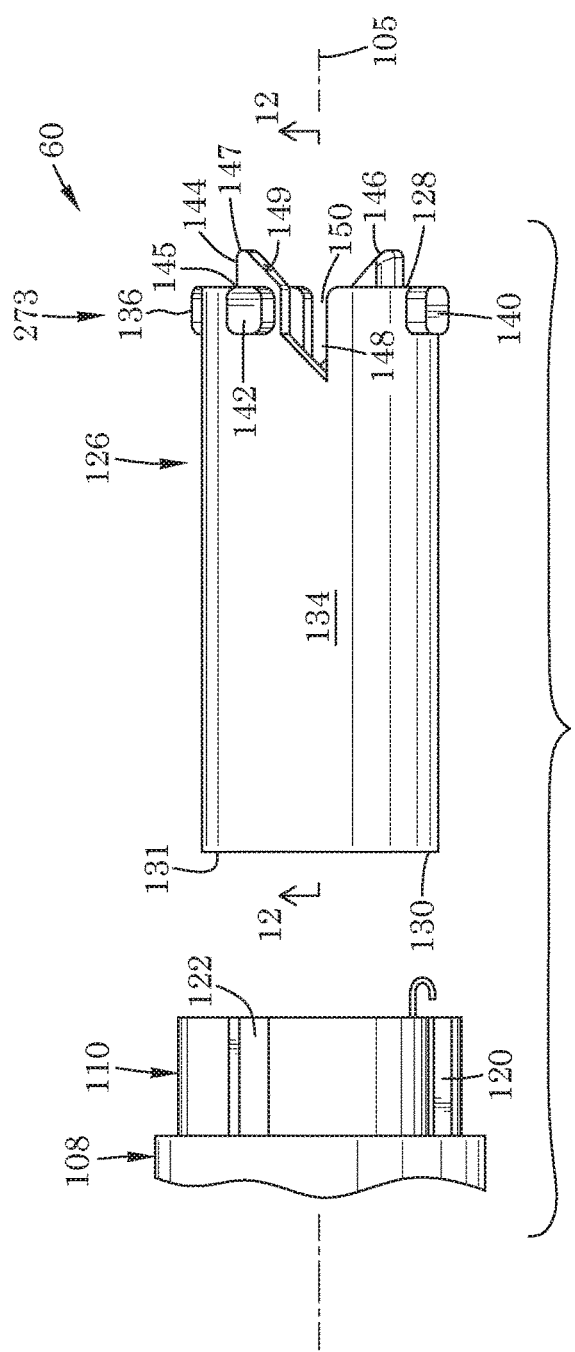
FIG. 9 is an exploded, side perspective view of the outer barrel and the inner barrel of FIG. 3, with the outer barrel being shown in fragment.

Referring to the drawings and first to FIG. 1, there is shown a protected needle assembly 60 for fitting to a syringe 62.

The syringe includes a hollow cylinder in this example a barrel 64 with graduation lines 66 thereon. The barrel is shaped to receive and retain a fluid 68 for administering to a patient 70 seen in FIG. 34 in this example via an arm 72. Referring to FIG. 1, the syringe 62 has a first or proximal end 74 and a second or distal end 76 between which barrel 64 extends. The term proximal as used in the description herein generally alludes to at or towards the gripping portion of a syringe and the term distal as used in the description herein generally alludes to at or towards a needle tip. The syringe 62 includes a finger flange 77 at the proximal end 74 thereof. The finger flange extends radially outwards relative to the barrel 64.

The syringe includes a piston, in this example a plunger 80. The plunger includes a thumb rest 82 at a first or proximal end 84 thereof and a plunger tip 86 at a second or distal end 88 thereof. The plunger 80 is shaped to slidably engage with and be received within the barrel 64. The plunger is moveable from an extended position shown in FIG. 1 to a depressed position shown in FIG. 40. Referring to FIG. 1, pushing inwards on the thumb rest 82 of the plunger 80 from right to left relative to FIG. 1 so as to cause the plunger tip 86 to move from the proximal end 74 of the syringe 62 towards the distal end 76 of the syringe functions to force fluid 68 out of the barrel 64 via said distal end of the syringe.

The syringe 62 includes a connection mechanism, in this example a Luer Lock™ tip comprising a sleeve 90 with interior threads 92 and a male fitting 94 which is coaxial with the sleeve. Syringes, Luer Locks™ and the like per se, including their various parts and functionings, are well known to those skilled in the art and thus will not be described in further detail.

As seen in FIG. 2, the protected needle assembly 60 has a top 96, bottom 98, a first or proximal end 100, a second or distal end 102, a pair of sides as shown by side 103 in FIG. 2 and a longitudinal axis 105 which extends between said ends. The assembly includes an adaptor, in this example a sleeve 104 at the proximal end thereof. The sleeve in this example is an annular, longitudinally-extending protrusion 106 shaped to threadably engage with the threads 92 of the sleeve 90 of the syringe 62 seen in FIG. 1. In this manner, the proximal end 100 of the assembly 60 selectively couples to the distal end 76 of the syringe.

As seen in FIG. 3, the protected needle assembly includes an outer barrel 108 that is generally tubular in shape. As seen in FIG. 2, the outer barrel has a first or proximal end 110 near the proximal end 100 of the assembly 60, and a second or distal end 112 adjacent to the distal end 102 of the assembly. The outer barrel has an annular outer surface 117 which extends between ends 110 and 112 and parallel to longitudinal axis 105 of the assembly 60. As seen in FIG. 4, the outer barrel 108 includes a male fitting 114 adjacent to the proximal end 110 thereof. The male fitting is radially inwardly recessed relative to the outer surface 117 of the outer barrel. The male fitting 114 extends in an axial direction along longitudinal axis 105 of the assembly 60. The outer barrel 108 includes an annular seat 115 adjacent to and radially outwardly-extending relative to the male fitting 114 in this example. The annular seat extends between the male fitting and annular outer surface 117 of the outer barrel in this example.

The outer barrel 108 has an interior 116 and a plurality of circumferentially spaced-apart, longitudinally-extending channels, in this example four channels 118, 120, 122 and 124 positioned within the interior. Each of the channels of the outer barrel 108 extends from the proximal end 110 of the outer barrel towards the distal end 112 of the outer barrel. Each of the channels 118, 120, 122 and 124 is generally a rectangular prism in shape, is smooth and is u-shaped in cross-section in this example. Each of the channels extends radially outwards from the interior 116 of the outer barrel 108 part way towards the outer surface 117 of the outer barrel in this example. Each of the channels 118, 120, 122 and 124 extends through male fitting 114 in this example. Referring to FIG. 7, each of the channels has an end 125 with a seat 127 located thereat.

Figure 11:
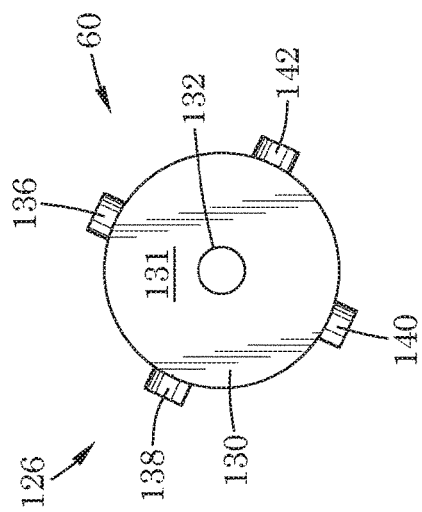
FIG. 11 is a distal end elevation view of the inner barrel of FIG. 9.

Referring now to FIG. 3, the protective needle assembly 60 includes an inner barrel 126. As seen in FIG. 9, the inner barrel is generally cylindrical in shape, and has a first or proximal end 128 and a second or distal end 130 that is generally closed. Referring to FIGS. 11 and 12, the inner barrel 126 includes an end wall 131 adjacent to the distal end 130 thereof. As seen in FIG. 11, the end wall is generally circular in this example and has a centrally-positioned, circular aperture 132 extending therethrough.

As seen in FIG. 9, the inner barrel 126 includes an annular outer wall 134 which extends between the ends 128 and 130 thereof and in parallel with longitudinal axis 105 of the assembly 60. As seen in FIG. 12, the outer wall couples to and is integrally formed with end wall 131 in this example. Still referring to FIG. 12, the inner barrel 126 has a central bore 135 which extends from the proximal end 128 thereof towards the distal end 130 thereof. The outer wall 134 extends around the central bore. Aperture 132 and bore 135 are coaxial and in communication with each other in this example.

Figure 10:
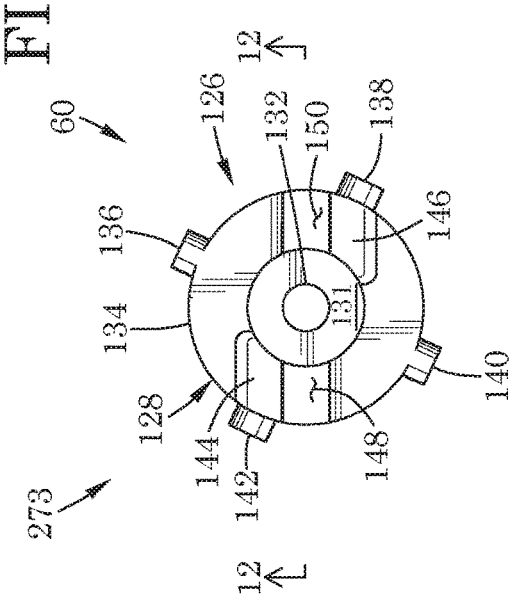
FIG. 10 is a proximal end elevation view of the inner barrel of FIG. 9.

As seen in FIG. 10, the inner barrel 126 includes a plurality of circumferentially spaced-apart protrusions, in this example four protrusions 136, 138, 140 and 142. As seen in FIG. 9, the protrusions are generally rectangular prisms in shape in this example and radially extend outwards from outer wall 134. The protrusions 136, 138, 140, and 142 are adjacent to and extend from the proximal end 128 of the inner barrel 126 towards the distal end 130 of the inner barrel.

Referring to FIG. 10, each of the protrusions 136, 138, 140 and 142 of the inner barrel 126 is shaped to slidably engage with the outer barrel 108 seen in FIG. 4 via a respective one of the channels 118, 120, 122 and 124 of the outer barrel. In this manner and referring to FIG. 3, the inner barrel is selectively disposable within the outer barrel. As seen in FIG. 35, the inner barrel 126 has an extended position in which the protrusions 140 and 142 abut the seats 127 of the channels of the outer barrel 108. In the extended position, the inner barrel extends axially outwards from the distal end 112 of the outer barrel and along longitudinal axis 105 of the assembly 60.

Figure 38:
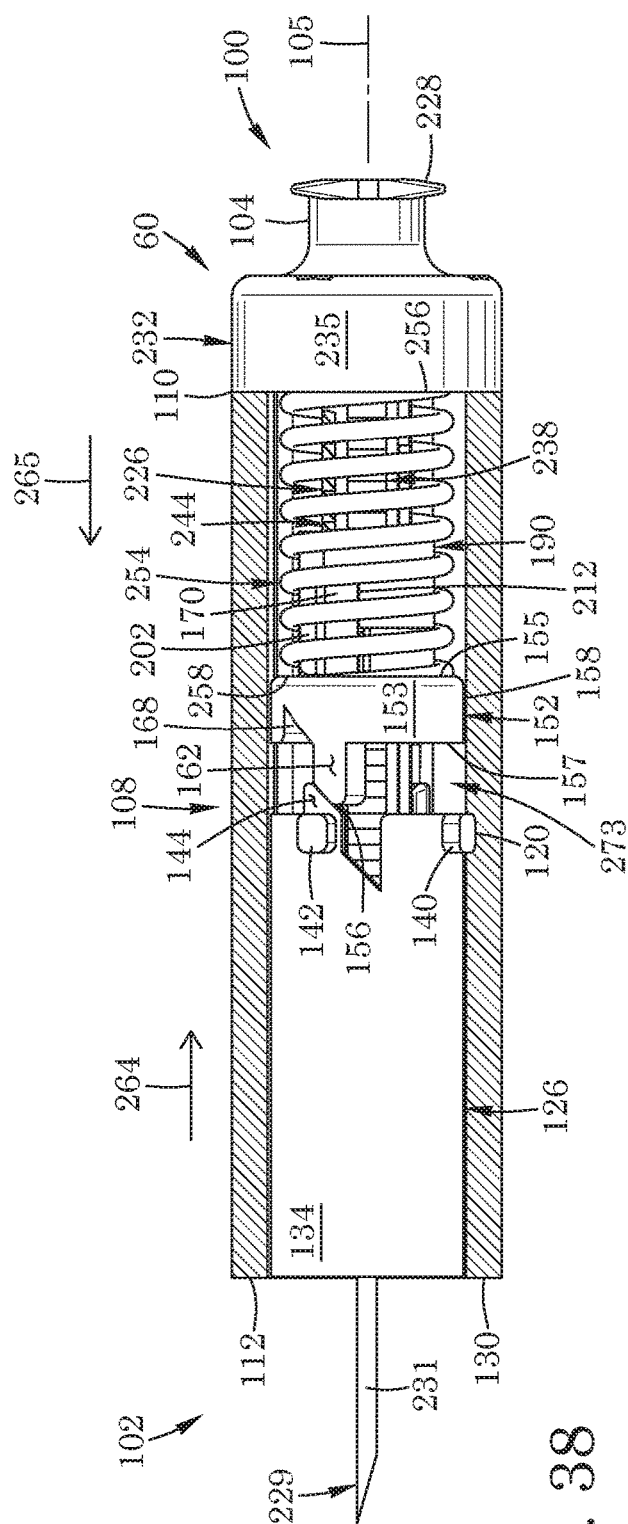
FIG. 38 is a side elevation view of the assembly and hypodermic needle of FIG. 37, with the right side half of the outer barrel of the assembly being removed to reveal positioning of the inner barrel, hub, latch member and spring in the needle-insertion mode according to said first aspect.

The inner barrel 126 is movable from the extended position seen in FIG. 35 to a retracted position seen in FIG. 38. The distal end 130 of the inner barrel aligns flush with the distal end 112 of the outer barrel 108 in the retracted position of the inner barrel in this example.

As seen in FIG. 9, the inner barrel 126 includes a pair of guide members 144 and 146. Each guide member is angled at least in part and in this example is beveled. Each of the guide members 144 and 146 is generally a triangular prism in shape in this example with bore 135, seen in FIG. 12, cutting therethrough. However, this is not strictly required and the guide members 144 and 146 can comprise other shapes in other embodiments. As seen in FIG. 9, the guide members 144 and 146 are triangular in side profile in this example. As seen in FIG. 10, the guide members 144 and 146 are circumferentially spaced-apart from each other by 180 degrees in this example. Referring to FIG. 9, the guide members couple to and extend axially outwards from the proximal end 128 of the inner barrel 126. The guide members 144 and 146 are integrally formed with and extend axially outwards from the outer wall 134 of the inner barrel 126 in this example. As seen in FIG. 9, each of the guide members 144 and 146 includes a first end 145 coupled to the outer wall 134 adjacent to the proximal end 128 of the inner barrel, a second end 147 axially spaced-apart along longitudinal axis 105 from the first end, and an angled, in this example bevelled, surface 149 which extends from the first end thereof to the second end thereof. As seen in FIG. 10, protrusion 142 is adjacent to guide member 144 and protrusion 138 is adjacent to guide member 146 in this example.

The inner barrel 126 includes a pair of rotation-locking recesses 148 and 150 positioned adjacent to respective ones of the guide members 144 and 146. The recesses are generally right trapezoids in shape in side profile in this example. As seen in FIG. 10, protrusion 142 is adjacent to recess 148 in this example, and protrusion 138 is adjacent to recess 150 in this example. As seen in FIG. 9, each of the recesses is in communication with the proximal end 128 of the inner barrel 126. Each of the recesses 148 and 150 extends from the proximal end of the inner barrel towards the distal end 130 of the inner barrel. As seen in FIG. 10, the guide members 144 and 146 are circumferentially spaced-apart from each other by 180 degrees in this example.

Referring to FIG. 3, the protected needle assembly 60 includes a hub 152 disposable within outer barrel 108, as seen in FIG. 35. As seen in FIG. 14, the hub has a first or proximal end 154 and a second or distal end 156. Referring to FIG. 15, the hub 152 includes an annular base 158 positioned between the ends 154 and 156 thereof. The annular base has an annular outer surface 153 which extends in parallel to longitudinal axis 105 of the assembly 60. The hub 152 includes a central bore 159 about which the annular base extends. Referring to FIG. 18, the base 158 has a first or proximal end 155 facing the proximal end 154 of the hub and a second or distal end 157 facing the distal end 156 of the hub.

As seen in FIG. 15, the distal end 157 of the base 158 of the hub 152 forms an inner-barrel seat in this example in the form of a pair of arc-shaped surfaces 161 and 163. The arc-shaped surfaces extend laterally from the outer surface 153 of the base 158 of the hub and extend laterally relative to longitudinal axis 105. As seen in FIG. 14, the arc-shaped surfaces 161 and 163 are configured to face the inner barrel 126. As seen in FIG. 15, the surfaces 161 and 163 of the base 158 of the hub 152 are circumferentially spaced-apart by 180 degrees in this example.

Still referring to FIG. 15, the hub includes at least one, and in this example a pair of circumferentially spaced-apart, distally-extending protrusions, in this case guide members 162 and 164. The guide members are spaced-apart by 180 degrees in this example and are generally right trapezoids in shape in side profile in this example. However, this is not strictly required and the guide members 162 and 164 can comprise other shapes in other embodiments. The guide members couple to and extend axially outwards relative to longitudinal axis 105 from surfaces 161 and 163, respectively, and distal end 157 of the base 158 to the distal end 156 of the hub 152 in this example. As seen in FIG. 15, each of the guide members 162 and 164 has a first end 165 which coincides with and is adjacent to the distal end 156 of the hub, a second end 167 axially spaced-apart from the first end, and an angled, in this example bevelled surface 169 which extends from the first end to said second end.

Still referring to FIG. 15, the hub 152 includes at least one, and in this example a pair of circumferentially spaced-apart recesses 166 and 168, each of which is triangular in side profile as seen in FIG. 16. However, this is not strictly required and the recesses can comprise other shapes in other embodiments. As seen in FIG. 15, recess 168 extends axially from surface 161 of base 158 of the hub 152 towards the proximal end 154 of the hub, and is positioned between said surface 161 and guide member 162 in this example. Recess 166 extends axially from surface 163 of the base of the hub towards the proximal end of the hub, and is positioned between said surface 163 and guide member 164 in this example. The recesses 166 and 168 are circumferentially spaced-apart by 180 degrees in this example.

As seen in FIG. 14, the hub 152 includes at least one, and in this example a pair of catches 170 and 172 which are circumferentially spaced-apart by 180 degrees in this example. The catches couple to and extend axially outwards from the proximal end 155 of the base 158 of the hub in this example to the proximal end 154 of the hub. As seen in FIG. 17, each of the catches 170 and 172 comprises a rotation-locking protrusion or elongate portion 174. Each of the catches has an outer end 176 that extends radially inwards towards longitudinal axis 105 of the assembly 60. Each of the outer ends of the catches 170 and 172 is at least partially hook-shaped and in this example triangular in side cross-section. The outer ends 176 of the catches coincide with and are adjacent to the proximal end 154 of the hub 152 in this example.

Referring to FIG. 14, the hub includes a pair of arcuate-shaped members 178 and 180 in this example which extend between the catches 170 and 172. The arcuate-shaped members have distal ends 182 which couple to and are integrally formed with the proximal end 155 of the base 158 of the hub in this example. The arcuate-shaped members 178 and 180 have proximal ends 184 which are axially spaced-apart along longitudinal axis 105 from the distal ends thereof. The proximal ends 184 of the arcuate-shaped members are positioned between the distal ends 182 of the arcuate-shaped members and proximal end 154 of the hub 152. The arcuate-shaped members 178 and 180 of the hub are radially inwardly positioned relative to the outer surface 153 of base 158 of the hub.

Referring to FIG. 16, the arcuate-shaped members 178 and 180 form a latch member seat in this example in the form of a pair of arc-shaped surfaces 186 and 188. The arc-shaped surfaces are adjacent to the proximal ends 184 of the members 178 and 180 and face opposite surfaces 161 and 163 of base 158 in this example.

As seen in FIG. 3, the assembly 60 includes an annular latch member 190 disposable within outer barrel 108, as seen in FIG. 36. Referring to FIG. 20, the latch member has a first or proximal end 192 and a second or distal end 194. Referring to FIG. 21, the latch member 190 includes an annular base 196 having a proximal end 198 which coincides with and is adjacent to the proximal end 192 of the hub. The base of the latch member has a distal end 200 axially-spaced apart along the longitudinal axis 105 from the proximal end thereof. The base 196 has an annular outer surface 197 which extends in parallel with longitudinal axis 105 of the assembly 60 in this example. The base 196 forms a hub seat comprising in this example a pair of arc-shaped surfaces 201 and 203. The arc-shaped surfaces are adjacent to the distal end 200 of the base 196 of the latch member 190 and face hub 152 seen in FIG. 20.

As seen in FIG. 21, the latch member includes at least one, and in this example a pair of catches 202 and 204 which are circumferentially spaced-apart by 180 degrees in this example. The catches operatively couple to and extend axially outwards relative to the longitudinal axis 105 from the base 196 of the latch member 190 in this example to the distal end 194 of the latch member. As seen in FIG. 22, each of the catches 202 and 204 comprises an elongate portion 206, with an outer end 208 that extends radially inwards relative to outer surface 197 of the base 196. Each of the outer ends of the catches is at least partially hook-like and, in this example, triangular in side cross-section. The outer ends 208 of the catches 202 and 204 coincide with and are adjacent to the distal end 194 of the latch member 190.

As seen in FIG. 21, the latch member has a first pair of circumferentially spaced-apart, rotation-locking recesses 210 and 212 between which is positioned catch 202. The latch member 190 has a second pair of circumferentially spaced-apart recesses 214 and 216 between which is positioned catch 204. Each of the recesses is rectangular in side profile in this example and extends from distal end 200 of the base 196 of the latch member 190 towards the proximal end 192 of the latch member in this example.

Still referring to FIG. 21, the base of the latch member includes a pair of circumferentially spaced-apart arc-shaped portions 218 and 220 positioned between recesses 212 and 214, and recesses 210 and 216, respectively. The arc-shaped portions extend from distal end 200 of the base 196 of the latch member 190 towards the proximal end 192 of the latch member in this example. As seen in FIG. 24, the latch member includes elongate protrusions 222 and 224 coupled to and radially inwardly-extending from respective ones of the arc-shaped portions 218 and 220 of the base thereof and towards longitudinal axis 105 of the assembly 60. Each of the protrusions is a rectangular prism in shape in this example and extends from the distal end 200 of the base 196 to the proximal end 192 of the latch member 190 in this example. However, it is not strictly required that protrusions 222 and 224 are rectangular prisms in shape, nor do the protrusions have to extend fully from end 200 to end 192, nor do the protrusions have to be spaced-apart from each other by 180 degrees, nor are two protrusions required as long as there is one or more protrusions.

As seen in FIG. 25, the protrusions 222 and 224 are circumferentially spaced-apart from each other by 180 degrees in this example. Protrusion 224 is circumferentially spaced-apart from catch 202 by an angle α, which is equal to 60 degrees in this example. Protrusion 222 is also circumferentially spaced-apart from catch 204 by angle α which is also equal to 60 degrees in this example. However, this is not strictly required and angle α may be different in other embodiments.

Referring now to FIG. 3, the assembly 60 includes a centrally-positioned elongate member 226. As best seen in FIG. 32, the elongate member has a first or proximal end 228 which coincides with and is adjacent to the proximal end 100 of the assembly. Sleeve 104 is a part of the elongate member 226 in this example and is located adjacent to the proximal end of the elongate member. The elongate member has a second or distal end 230 that is axially spaced-apart along longitudinal axis 105 of the assembly 60 from the proximal end thereof.

As seen in FIG. 32, the elongate member 226 includes a female connector 232 comprising a tubular portion 235 with an open end 237 and a closed end 239 along which extends an annular flange 241. The flange of the female connector is coupled to, integrally formed with, and extends radially outwards relative to sleeve 104. The tubular portion 235 of the female connector 232 is coaxial with the sleeve in this example. Referring to FIG. 3, the female connector is distally-facing and shaped to frictionally engage with, receive and extend about the male fitting 114 of the outer barrel 108 to couple the elongate member 226 to the outer barrel. As seen in FIG. 4, the outer barrel 108 includes an outwardly-facing, hook-shaped latch 249 coupled to and extending outwards from the distal end of the male fitting 114 of outer barrel 108. The latch engages a recess 251 in the female connector 232 seen in FIG. 33B. The recess is complementary in shape to the hook shaped latch 249 of male fitting 114 seen in FIG. 4, and the latch so engaged with the recess locks elongate member 226 to outer barrel 108 in this example. Referring to FIG. 2, the proximal end 228 of the elongate member 226 thus operatively couples with the proximal end 110 of the outer barrel 108. As seen in FIG. 3, the elongate member 226 is co-axial with the outer barrel in this example.

Referring to FIG. 28, the elongate member 226 has a central bore 234 which extends from the proximal end 228 to the distal end 230 thereof. The elongate member includes a shaft portion 236 coupled to and axially extending from flange 241 of the female connector 232 to the distal end 230 of the elongate member.

As seen in FIG. 30, a hypodermic needle 229 is selectively connectable to the distal end 230 of the elongate member. Referring to FIG. 27, the needle is configured to be co-axial with longitudinal axis 105 of the assembly 30. Referring to FIG. 12, aperture 132 of the inner barrel 126 is shaped to receive the shaft 231 of the needle 229 seen in FIG. 32 therethrough. Referring back to FIG. 30, the hypodermic needle includes a connection mechanism, in this example a Luer Lock™ tip type mechanism 233 for selectively coupling the hypodermic needle to the distal end 230 of the elongate member 226. Luer Locks™ and the like per se, including their various parts and functionings, are well known to those skilled in the art and thus will not be described in further detail.

The elongate member 226 includes a plurality of circumferentially spaced-apart, longitudinally-extending, outwardly-facing channels that extend along the shaft portion 236 thereof which extend from adjacent to the open end 237 of the female connector 232 towards the distal end 230 of the elongate member. Referring to FIG. 28, these channels include a first pair of circumferentially spaced-apart channels 238 and 240 which are serrated and spaced-apart by 180 degrees in this example. The channels include longitudinally-extending serrated edge portions 242 and 243. Referring to FIG. 3, the catches 170 and 172 of the hub 152 are shaped to engage with the serrated edge portions 242 and 243 when the hub is in a post-injection angular position as seen in FIGS. 43 to 47. The catches and channels 238 and 240 are configured to inhibit retraction of the hub 152 towards the proximal end 100 of the assembly 60. The catches 170 and 172 and channels 238 and 240 are configured to enable axial movement of the hub in a direction moving along longitudinal axis 105 from the proximal end of the assembly towards the distal end 102 of the assembly.

Referring to FIGS. 27 and 30, the channels includes a pair of channels 244 and 245 which are serrated. As seen in FIG. 33A, channels 244 and 245 are circumferentially spaced-apart by 180 degrees in this example. Channel 244 is circumferentially spaced-apart by an angle α from channel 238. In this example angle α is equal to 60 degrees. Channels 244 and 245 each include a longitudinally-extending serrated edge portion, as seen in FIG. 32 by edge portion 246 for channel 244 and as seen in FIG. 33E by edge portion 247 for channel 245. Referring to FIG. 3, selective ones of the catches of the latch member 190 are shaped to engage with the serrated edge portions 246 and 247, in this example catch 202 as seen in FIG. 36. Still referring to FIG. 36, the catches of the latch member and channel 244 are configured to enable movement of the latch member towards the proximal end 110 of the outer barrel 108 and to inhibit movement of the latch member towards the distal end 112 of the outer barrel.

As seen in FIG. 27, the shaft portion 236 of the elongate member 226 has a longitudinally-extending, smooth outer surface, in this example a pathway 260 positioned between channels 238 and 244 in this example. As seen in FIG. 30, the shaft portion of the elongate member has a second longitudinally-extending, smooth outer surface, in this example a pathway 261 positioned between channels 240 and 245. As seen in FIG. 33A, the pathways 260 and 261 are circumferentially spaced-apart by 180 degrees in this example.

As seen in FIGS. 31 and 32, the channels includes a pair of circumferentially spaced-apart channels 250 and 252. These channels are smooth and u-shaped in cross-section in this example. As seen in FIG. 33A, channels 250 and 252 are circumferentially spaced-apart by 180 degrees in this example. Referring to FIG. 21, the protections 222 and 224 of the latch member 190 are shaped to engage with respective ones of the channels 250 and 252. The projections and channels function to hold the latch member 190 in place so as to inhibit rotation of the latch member and promote engagement of selective ones of the catches thereof with channel 244 seen in FIG. 27.

As seen in FIG. 3, the assembly 60 includes a resilient member, in this example a coil spring 254. The spring has a first or proximal end 256 received within the female connector 232 of the elongate member 226. The spring 254 has a second or distal end 258 axially spaced-apart from the proximal end thereof. As seen in FIG. 35, the distal end of the spring abuts the proximal end 155 of the base 158 of the hub 152. The spring 254 extends around and remains free of the latch member 190. The spring is configured to bias the hub 152 and the inner barrel 126 towards the distal end 112 of the outer barrel 108 and in the outwards direction as shown by arrow of numeral 272.

In operation, the assembly 60 is shown in FIG. 35 with the inner barrel 126, hub 152, latch member 190 and spring 254 in a pre-injection mode. The spring is in a partially extended state. The protrusions 140 and 142 of the inner barrel are abutting the seats 127 of the channels 120 of the outer barrel 108. The inner barrel 126 extends outwards from the distal end 112 of the outer barrel and extends about hypodermic needle 129 so as to enclose the same. The inner barrel as shown may be referred to as being in a protected needle mode. As seen in FIG. 36, each of the catches 170 of the hub 152 is slidably engageable with a respective pathway 260 of the elongate member 226 to move distally or proximally in the pre-injection mode in an injection angular position which is circumferentially spaced-apart from serrated channels 238.

As seen in FIG. 35, the hub 152 is outwardly/distally biased in the direction shown by arrow of numeral 272. The hub is positioned such that its guide members 162 abut the corresponding guide members 144 of the inner barrel 126. As seen in FIG. 36, the catches 202 of the latch member 190 engage with respective serrated edge portions 246 of serrated channels 244. The latch member so positioned enables the latch member to retract towards the proximal end 100 of the assembly 60 and inhibits the latch member from moving towards the distal end 102 of the assembly. Still referring to FIG. 36, the recesses 212 of the latch member 190 are shaped to receive respective ones of the catches 170 of the hub 152. In this manner and mode, rotation and thus inadvertent dislodgement of the hub from pathways 260 is inhibited. In this mode, the needle 129 is enclosed within inner barrel 126 and accidental and/or inadvertent piercing of persons with the needle is thereby inhibited.

Figure 37:
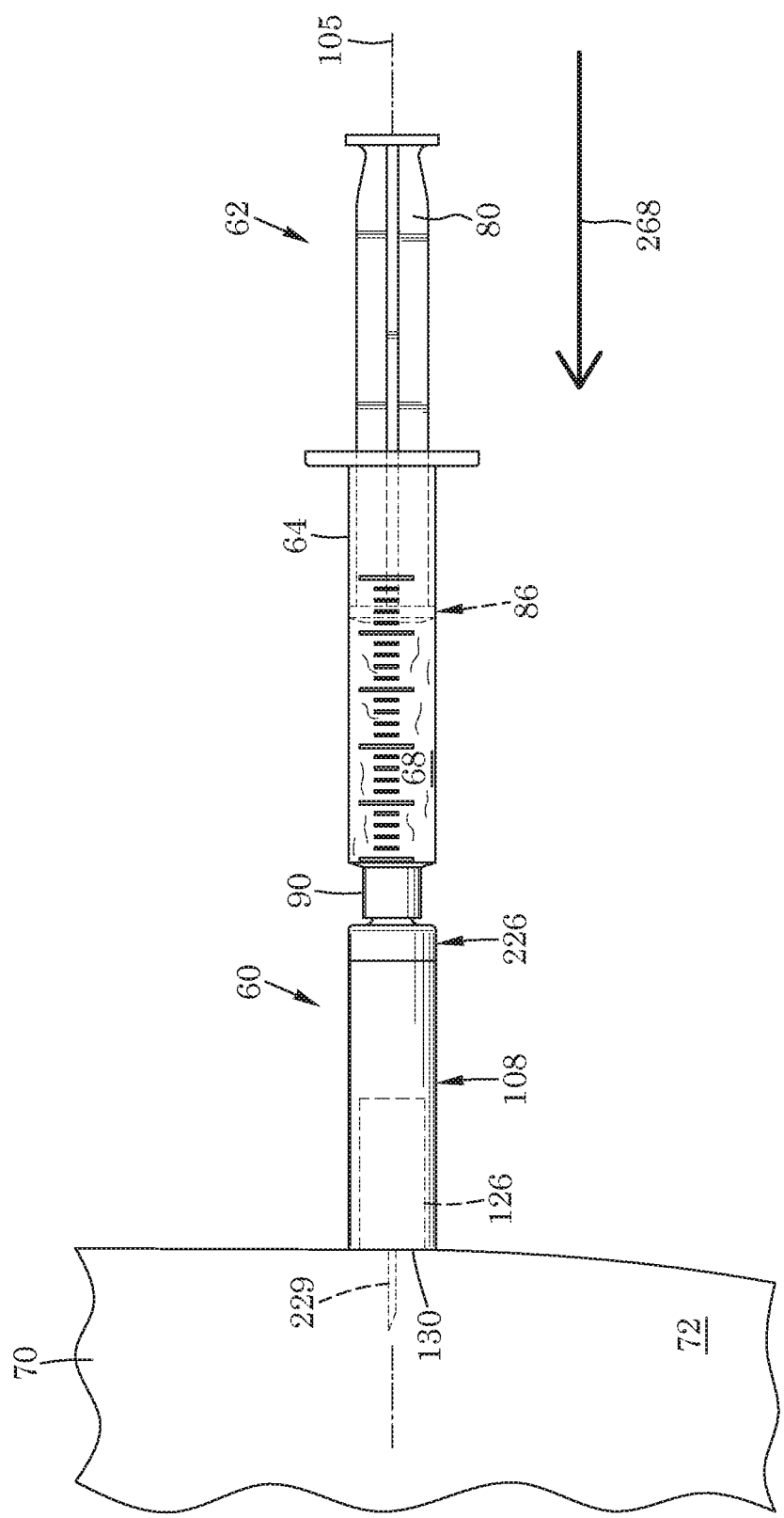
FIG. 37 is a side elevation view of the syringe, the protected needle assembly and hypodermic needle of FIG. 34 in a needle-insertion mode according to a first aspect, with the hypodermic needle being shown in ghost and inserted into the patient's arm, and with the inner barrel of the assembly being retracted within the outer barrel.
Figure 39:
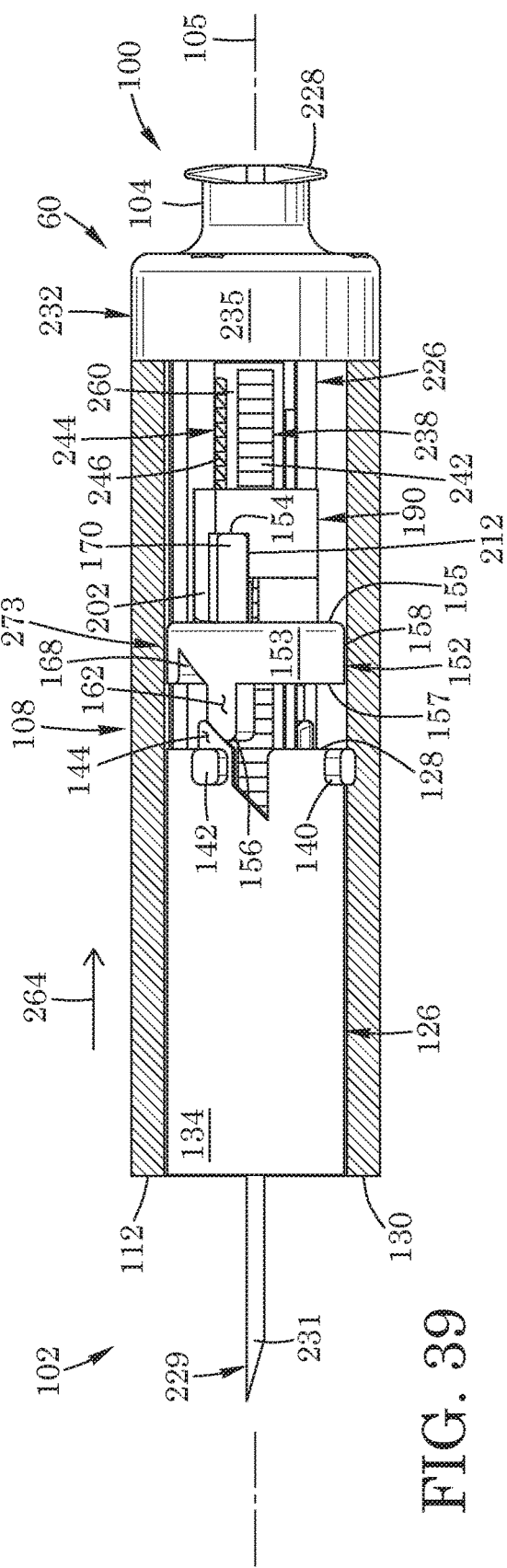
FIG. 39 is a side elevation view of the assembly and hypodermic needle of FIG. 37, with the right side half of the outer barrel and the spring of the assembly being removed to reveal positioning of the inner barrel, hub and latch member in the needle-insertion mode according to said first aspect.

As seen in FIG. 34, the inner barrel 126 is shaped to abut the arm 72 of patient 70. The person administering the injection thereafter pushes the assembly 60 towards the arm, as shown by arrow of numeral 262. This causes the inner barrel 126 to retract within outer barrel 108 as the needle 229 pierces the patient's arm as shown in FIG. 37. The assembly 60 is thus configured such that any exposure of the needle is inhibited, with the inner barrel only retracting when the needle is already inserted into the patient's body. Referring to FIG. 39, retraction of the inner barrel 126, as shown by arrow of numeral 264, causes the guide members 144 of the inner barrel to abut the guide members 162 of the hub 152, which functions to cause catches 170 of the hub to abut the latch member 190. In this manner and referring to FIG. 38, the outwardly biasing force 265 of the spring 254 is overcome, the spring compresses, and the inner barrel 126, hub 152 and latch member 190 retract towards the proximal end 100 of the assembly 60.

Figure 40:
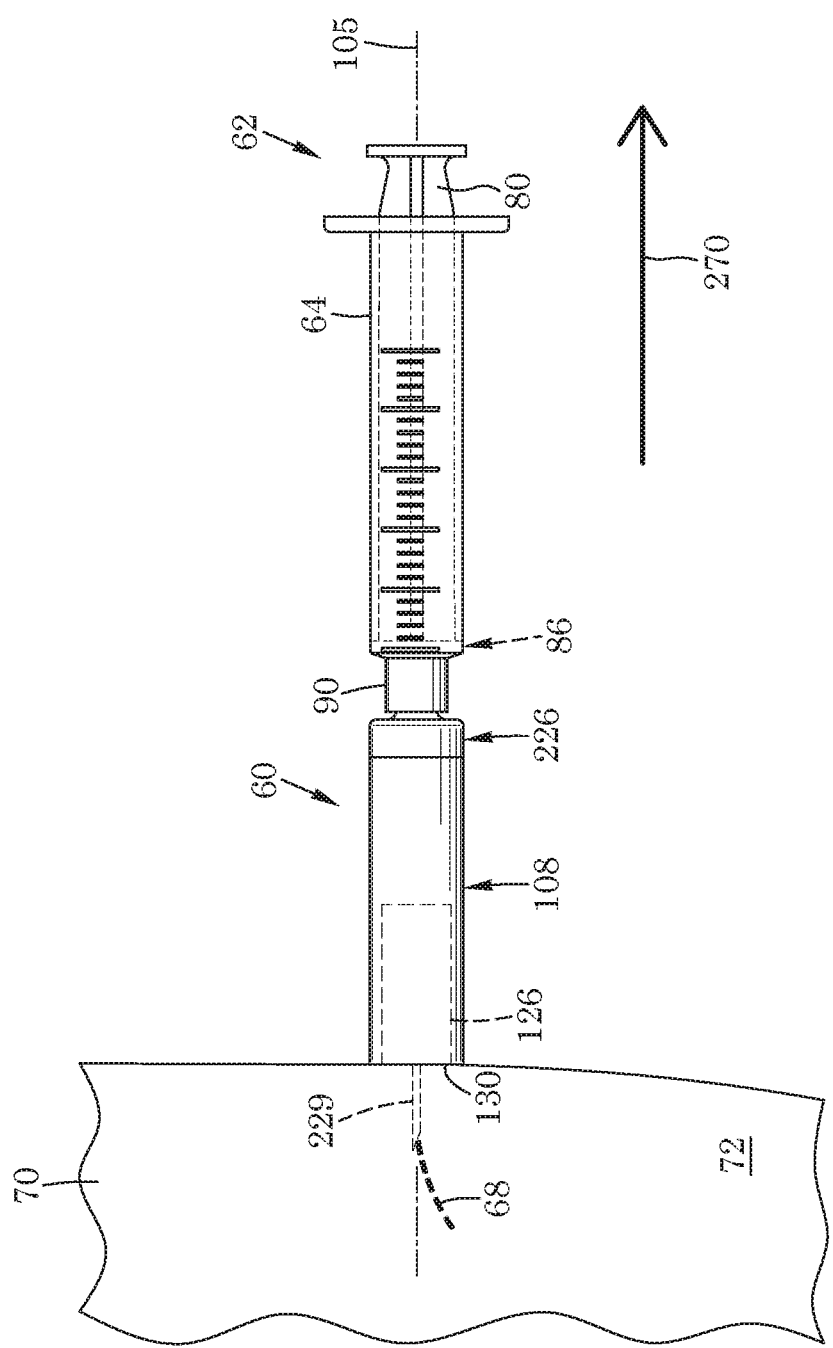
FIG. 40 is a side elevation view of the syringe, the protected needle assembly and hypodermic needle of FIG. 37 in an injection mode, with the hypodermic needle being shown in ghost and inserted with the patient's arm, with the inner barrel of the assembly being retracted within the outer barrel and with the plunger of the syringe being fully pushed into the barrel of the syringe so as to administer a fluid from the barrel of the syringe to the patient.

Referring to FIG. 37, the plunger 80 may now be depressed, as shown by arrow of numeral 268, to administer the fluid 68 from the barrel 64 of syringe 62 into the patient 70, as shown in the injection mode of FIG. 40.

Figure 41:
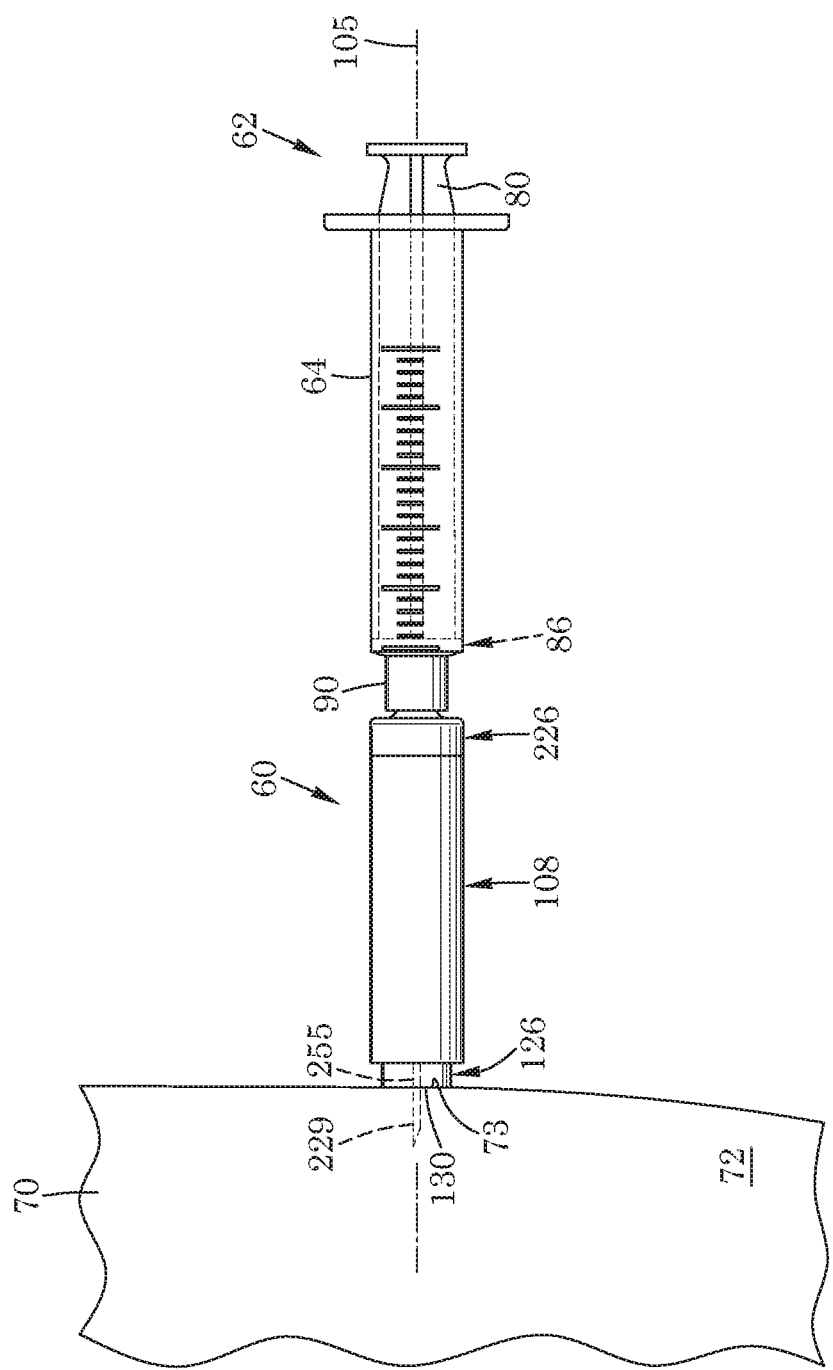
FIG. 41 is a side elevation view of the syringe, the protected needle assembly and hypodermic needle of FIG. 40 in a post-injection mode, with the hypodermic needle being shown in ghost and partially removed from the patient's arm, and with the inner barrel of the assembly abutting the patient's arm and partially extending outwards from the outer barrel of the assembly so as to extend about a removed portion of the hypodermic needle.
Figure 42:
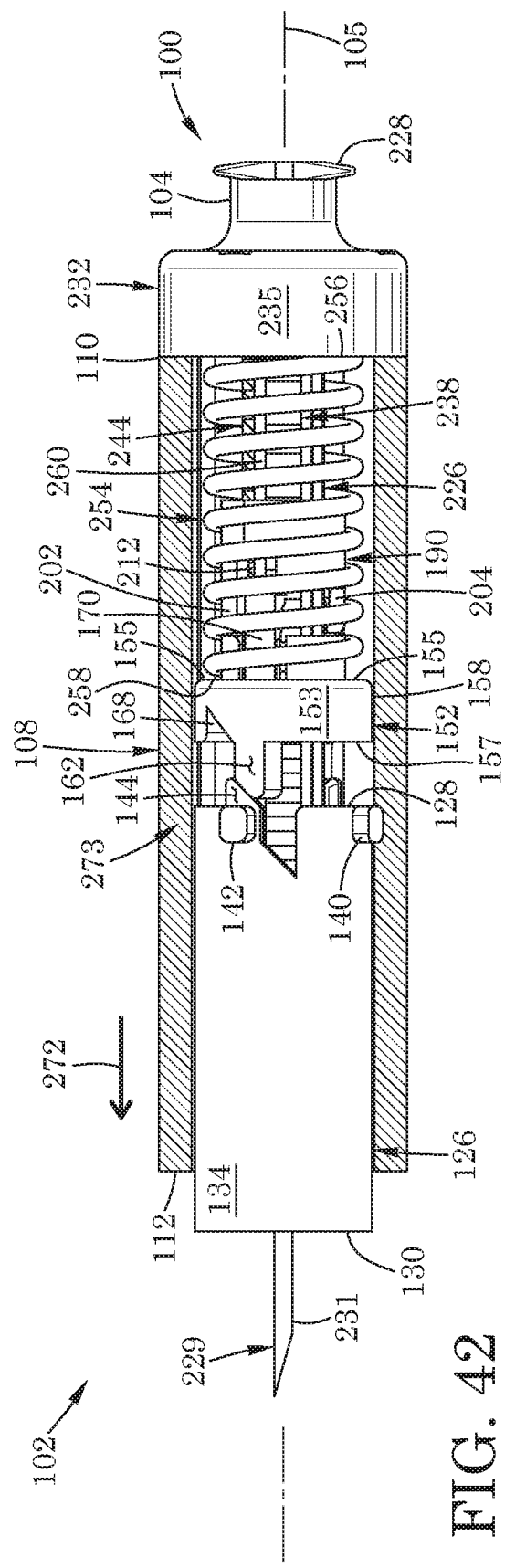
FIG. 42 is a side elevation view of the assembly and hypodermic needle of FIG. 41, with the hypodermic needle being shown partially in ghost, with the right side half of the outer barrel of the assembly being removed to reveal positioning of the inner barrel, hub, latch member and spring in the post-injection mode, and with the hub shown disengaged from the latch member, abutting guide members of the inner barrel and being shown in an injection angular position.

Upon the injection being complete and still referring to FIG. 40, the assembly 60 is pulled away from the arm 72 of the patient 70, as shown by arrow of numeral 270, and moves towards a post-injection mode. Referring to FIG. 42, this causes the shaft 231 of the needle 229 to be removed from the patient's arm, while at the same time enabling the spring 254 to outwardly bias and move the hub 152 and inner barrel 126 distally such that the inner barrel encloses portions of the needle removed from the arm once more. This is shown in FIG. 41 with the portion 255 of the needle 229 that is removed from arm 72 being enclosed by inner barrel 126 and skin 73 of the arm adjacent thereto. Exposure of the needle thus continues to be inhibited.

Figure 43:
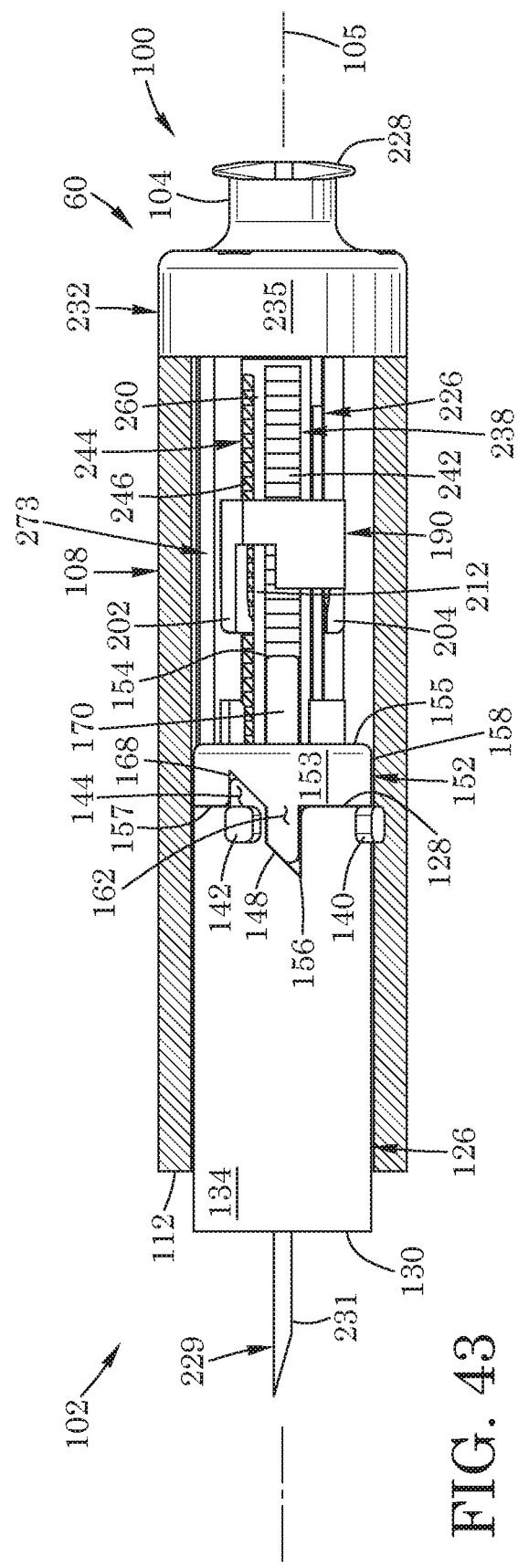
FIG. 43 is a side elevation view of the assembly and hypodermic needle of FIG. 41, with the hypodermic needle being shown partially in ghost, with the right side half of the outer barrel and the spring of the assembly being removed to reveal positioning of the inner barrel, hub, latch member and spring in the post-injection mode, and with the hub shown disengaged from the latch member and in a post-injection angular position in which retraction of the inner barrel towards the proximal end of the assembly is inhibited.
Figure 44:
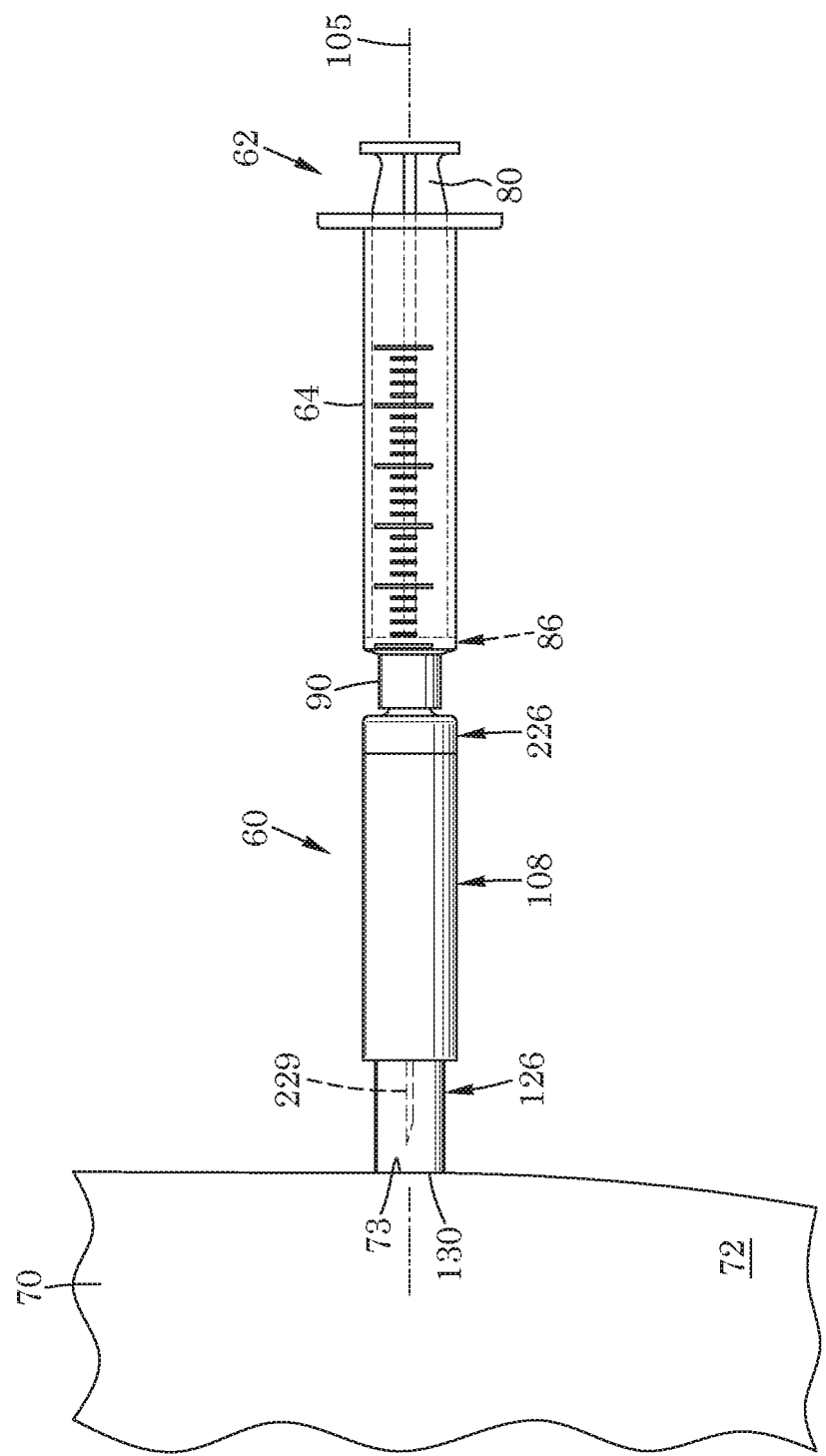
FIG. 44 is a side elevation view of the syringe, the protected needle assembly and hypodermic needle of FIG. 41 in the post-injection mode, with the hypodermic needle shown partially in ghost and fully removed from the patient's arm, and with the inner barrel of the assembly abutting the patient's arm and fully extending outwards from the outer barrel of the assembly so as to extend about the hypodermic needle so fully removed.
Figure 47:
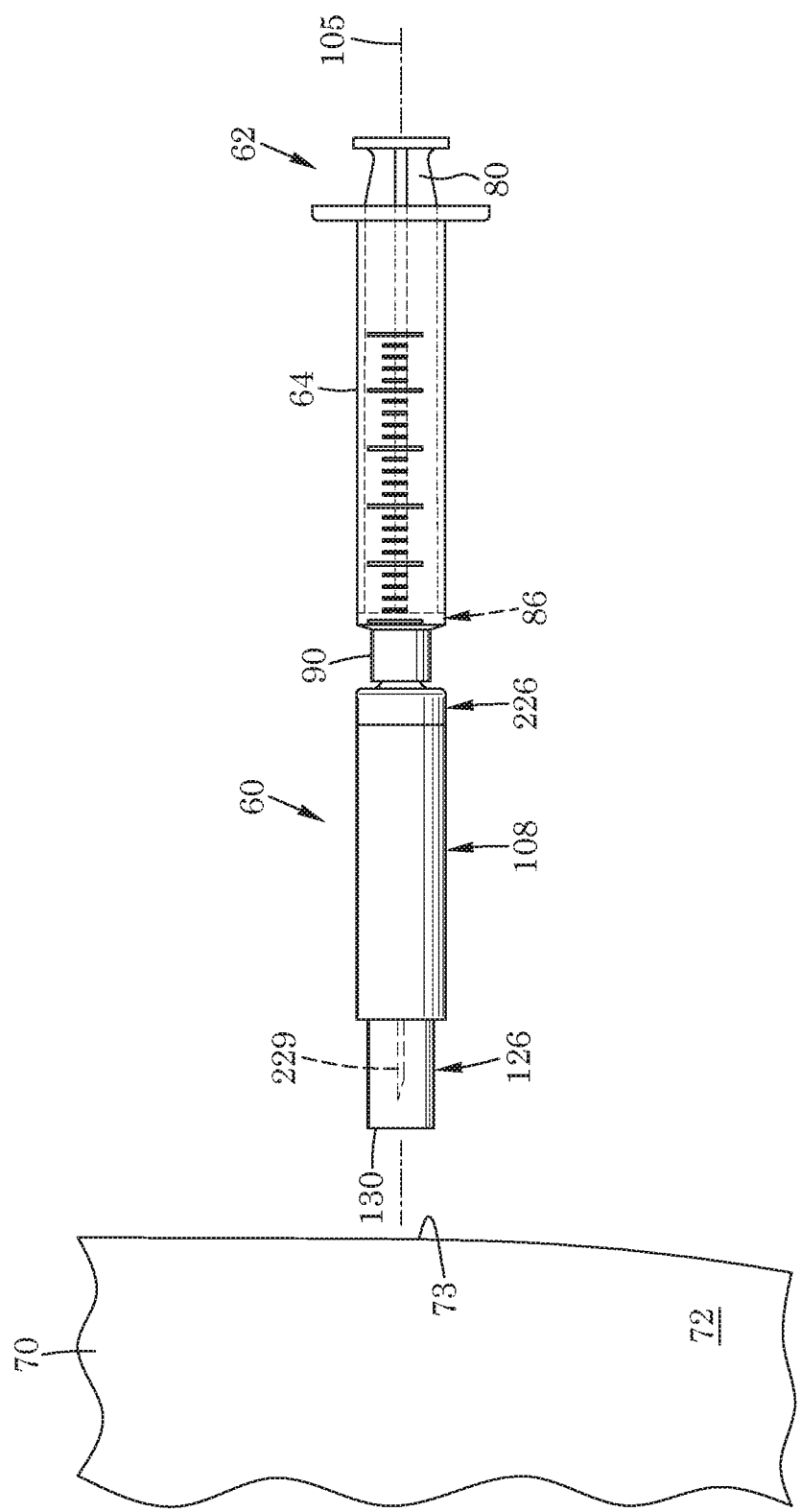
FIG. 47 is a side elevation view of the syringe, the protected needle assembly and hypodermic needle of FIG. 44 in the post-injection mode, with the hypodermic needle shown partially in ghost and spaced-apart from the patient's arm, and with the inner barrel of the assembly fully extending outwards from the outer barrel of the assembly so as to extend about the hypodermic needle so fully removed.

Referring to FIG. 43, the catches 202 of latch member 190 and serrated edge portions 246 of serrated channels 244 of the elongate member 226 so engaged with each other function to retain the axial position of the latch member 190 and inhibit the latch member from moving towards the distal end 112 of the outer barrel 108. Referring to FIG. 42, as spring 254 continues to move hub 152 axially towards the distal end 112 of the outer barrel 108, the catches 170 of the hub 152 eventually dislodge from recess 212 of the latch member.

In this manner and still referring to FIG. 42, a biasing force caused by the spring 254 against the guide members 162 of the hub 152, as generally shown by arrow of numeral 272, together with the angled shapes of the guide members 144 of the inner barrel 126, as well as the angled shapes of the guide members of the hub, promotes angular rotation of the catches 170 of the hub 152 from pathways 260 towards the serrated channels 238 seen in FIG. 43. This causes the hub to rotate from its pre-injection angular position, seen in FIGS. 35, 36, 38, 39 and 42, to a post-injection angular position seen in FIGS. 43, 45 and 46.

In the post-injection angular position and referring to FIG. 43, the guide members 162 of the hub 152 are shaped to fit within the recesses 148 of the inner barrel 126. This functions to inhibit any further rotation or dislodgment of the catches 170 of the hub 152 from serrated channels 238. Thus, once depression of plunger 80 seen in FIG. 37 has occurred and the assembly 60 is in the process of being removed from the patient 70 with the inner barrel 126 moving outwards from outer barrel 108 as seen in FIG. 43, latch member 190 and hub 152 function to prevent further exposure of the needle 229 and thereby inhibit needle injuries.

In the post-injection angular position and still referring to FIG. 43, the catches 170 of the hub 152 engage with the serrated edge portions 242 of serrated channels 238. This functions to enable movement of the inner barrel 126 and hub 152 towards the distal end 112 of the outer barrel and inhibit any further retraction of the hub and thus of the inner barrel 126. In this manner and referring to FIG. 46, retraction of the inner barrel 126 due to inadvertent re-application of retraction force 263 against the inner barrel is inhibited and the needle 229 thus enclosed and protected.

Figure 48:
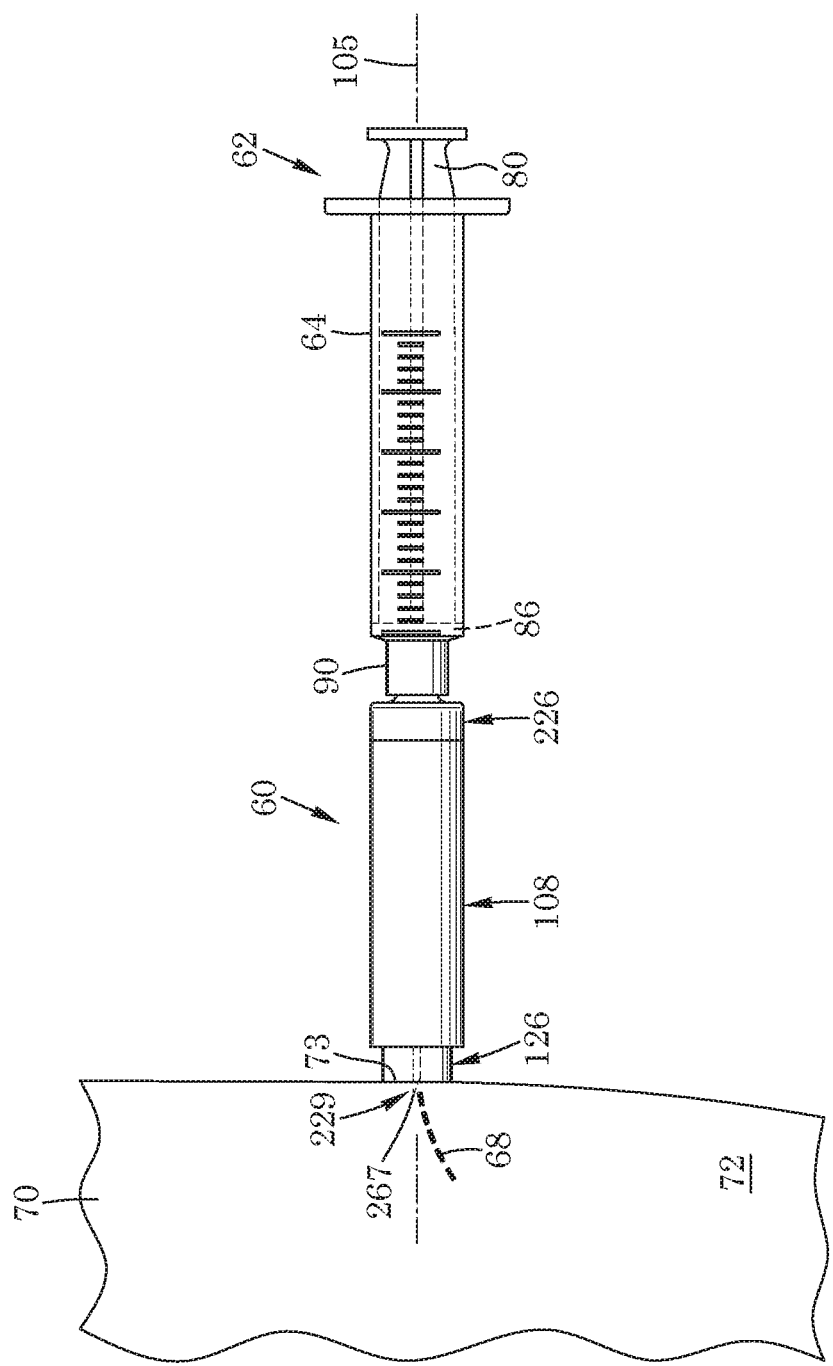
FIG. 48 is a side elevation view of the syringe, the protected needle assembly and hypodermic needle of FIG. 34 in a needle-insertion mode according to a second aspect in which only a tip portion of the needle is inserted into the patient's arm, with the needle being shown in ghost and with the inner barrel of the assembly being only partially retracted within the outer barrel.

FIG. 48 shows a variation in use of the assembly 60 in which just the tip portion 267 of needle 229 is inserted into the arm 72 of the patient 70. Inner barrel 126 is thus only partially retracted within outer barrel 108 of the assembly. Referring to FIG. 49, latch member 190 via the catch members 202 thereof and serrated edge portions 246 of channel 244 moves into a position that is more forward and closer to distal end 112 of outer barrel 108 in this example compared to the position of the latch member shown in FIG. 39 where the inner barrel is fully retracted within the outer barrel. Referring back to FIG. 49, when the injection is complete, the assembly is pulled away from the patient's arm, as shown by arrow of numeral 269. Latch member 190, via its catch members 202 engaging with channel 244, is inhibited from movement towards the distal end 112 of the outer barrel 108.

As the assembly 60 is pulled away from the patient and as seen in FIG. 50, spring 254 causes hub 158 and inner barrel 126 to move outwards towards the distal end of the outer barrel, as shown by arrow of numeral 271, whereupon catches 170 disengage from the recesses 212 of latch member 190, with the hub 152 thereafter rotating such that catches 170 engage with serrated edge portions 242 of channels 238 in a like manner as described above. The catches of the hub enable the hub and inner barrel to continue move outwards to enclose the needle and inhibit the inner barrel from retracting to expose the needle any further.

Thus, the assembly 60 as herein described, including its locking mechanism 273 of catches 202 of latch member 190, serrated channels 244, catches 170 of the hub 152 and serrated channels 238, functions to inhibit needle injury regardless of the depth of injection of the needle. Locking mechanism of the assembly may therefore lock into place at any depth of injection. Locking mechanism 273 as herein described is thus actuated upon the inner barrel 126 moving towards its protected needle mode once more and configured to inhibit further retraction of the inner barrel thereafter.

The hub 152, latch member 190, related catches and the serrated channels of the elongate member 226 may be referred to as a catch and serrated channel system.

It will be understood by someone skilled in the art that many of the details provided above are by way of example only and are not intended to limit the scope of the invention which is to be determined with reference to at least the following claims.

What is claimed is:

1. A protected needle assembly having a longitudinal axis and comprising:
   a longitudinally-extending outer barrel receiving a needle therethrough;
   a longitudinally-extending inner barrel resiliently biased to extend about the needle in a protected needle mode; and
   a catch and serrated channel system configured to enable the inner barrel to at least partially retract into the outer barrel to deploy the needle for a one-time use, with subsequent retraction of the inner barrel being inhibited, wherein the catch and serrated channel system includes one or more channels which are longitudinally-extending, within the one or more channels including a continuous plurality of laterally-extending serrated edge portions therewithin.

2. The assembly as claimed in claim 1 wherein the catch and serrated channel system is enclosed within the outer barrel.

3. The assembly as claimed in claim 1 wherein the one-time use of the needle comprises the inner barrel retracting anywhere in the range of the protected needle mode to a fully retracted position in which the inner barrel is fully retracted within the outer barrel, and wherein the catch and serrated channel system inhibits subsequent retraction of the inner barrel.

4. A protected needle assembly comprising:
   an outer barrel receiving a needle therethrough;
   an inner barrel resiliently biased to extend about the needle in a protected needle mode and being retractable into the outer barrel in a first instance to deploy the needle, with the inner barrel moving towards the protected needle mode thereafter; and
   a locking mechanism configured to inhibit further retraction of the inner barrel into the outer barrel thereafter, the locking mechanism being configured to activate anywhere in the range of a needle-insertion mode in which the inner barrel is only partially retracted within the outer barrel and only a tip portion of the needle is exposed, to a fully retracted position in which the inner barrel is fully retracted within the outer barrel.

5. The assembly as claimed in claim 4 wherein the locking mechanism includes a latch member coupled to the inner barrel when the inner barrel retracts within the outer barrel in the first instance, with the latch member decoupling from the inner barrel upon the inner barrel moving towards the protected needle mode thereafter.

6. The assembly as claimed in claim 4 wherein the locking mechanism includes a pair of members positioned within the outer barrel and coupled together when the inner barrel retracts within the outer barrel in the first instance, with a first said member disengaging from a second said member and coupling with the inner barrel upon the inner barrel moving towards the protected needle mode thereafter.

7. The assembly as claimed in claim 4 wherein the locking mechanism is configured to enable the inner barrel when pushed against a patient to at least partially retract into the outer barrel initially and inhibits further retraction of the inner barrel when the outer barrel is pulled away from the patient thereafter.

8. The assembly as claimed in claim 4 wherein the outer barrel has a first end through which the needle extends and a second end connectable to a syringe and wherein the inner barrel telescopically couples to and is biased outwards from the second end of the outer barrel, whereby pushing of the inner barrel against a patient causes the inner barrel to selectively retract into the outer barrel and at least a part of the needle to be inserted into the patient for injection of medicament, and pulling the outer barrel away from the patient thereafter causes the inner barrel to move to a post-injection mode in which the inner barrel extends about the needle and further retraction of the inner barrel into the outer barrel is inhibited.

9. The assembly as claimed in claim 4 wherein the locking mechanism includes a hub positioned within the outer barrel and retracting with the inner barrel in said first instance in an injection position, whereby movement of the inner barrel thereafter back towards the protected needle mode causes the hub to rotate to a post-injection position in which retraction of the inner barrel is inhibited.

10. The assembly as claimed in claim 8 wherein one of the inner barrel and the hub includes at least one beveled surface shaped to promote rotation of the hub to the post-injection position.

11. The assembly as claimed in claim 8 further including a centrally-positioned elongate member, the elongate member including at least one channel through which the hub slidably engages with the outer barrel in the injection position, and the elongate member including at least one longitudinally-extending serrated edge portion which is circumferentially spaced from the channel and via which the hub engages in the post-injection position.

12. The assembly as claimed in claim 8 wherein the outer barrel has a first end through which the needle extends, a second end connectable to a syringe, and an interior, wherein the outer barrel includes at least one channel positioned within said interior, the channel of the outer barrel extending from adjacent the first end of the outer barrel towards the second end of the outer barrel, and wherein the inner barrel includes at least one radially outwardly-extending protrusion shaped to slidably engage with the channel of the outer barrel.

13. The assembly as claimed in claim 8 wherein the inner barrel includes at least one guide member that is angled at least in part, the guide member being shaped to promote angular rotation of the hub from the injection position to the post-injection position.

14. The assembly as claimed in claim 8 wherein the inner barrel includes at least one recess shaped to receive a portion of the hub when the hub is in the post-injection position and wherein the hub is rotatable to the post-injection position via a spring force.

15. The assembly as claimed in claim 4 wherein the locking mechanism activates in the needle-insertion mode in which the inner barrel is only partially retracted within the outer barrel and only the tip portion of the needle is exposed and the inner barrel thereafter moves towards the needle protected mode, with further retraction of the inner barrel relative to the outer barrel being inhibited.

16. The assembly as claimed in claim 4 wherein the locking mechanism functions to inhibit needle injury regardless of the depth of injection of the needle.

17. The assembly as claimed in claim 4 wherein the locking mechanism locks into place at any depth of injection, with the depth of injection being determined by the extent to which the inner barrel is retracted into the outer barrel.

18. The assembly as claimed in claim 4 wherein the locking mechanism locks into place regardless of the extent of retraction of the inner barrel relative to the outer barrel.

19. A protected needle assembly comprising:
an outer barrel receiving a needle therethrough;
an inner barrel resiliently biased to extend about the needle in a protected needle mode; and
a locking mechanism including a pair of serrated channels, a hub and a latch member, whereby the inner barrel, the hub and the latch member selectively retract towards a proximal end of the outer barrel to deploy the needle, with the latch member thereafter being held in place via a catch thereof engaging a first said serrated channel, with the inner barrel thereafter being resiliently biased to extend about the needle in the protected needle mode once more, and with the hub being resiliently biased towards a second said serrated channel, which functions to inhibit retraction of the hub and the inner barrel towards the proximal end of the outer barrel thereafter.

20. A protected needle assembly comprising:
an outer barrel having a first end operatively connectable with a syringe and an open second end shaped to receive a hypodermic needle therethrough;
a centrally-positioned elongate member about which the outer barrel extends, the elongate member having a first end coupled to the first end of the outer barrel, being co-axial with the outer barrel, and having a second end to which the hypodermic needle is connectable, the elongate member including a smooth surface, a first serrated channel and a second serrated channel, the smooth surface and the channels being outwardly-facing, longitudinally-extending and circumferentially spaced-apart from each other;
an inner barrel slidably engageable with and outwardly biased towards the second end of the outer barrel so as to extend about the needle, the inner barrel including a guide member that is angled at least in part;
a hub disposed within the outer barrel and outwardly biased to abut the guide member of the inner barrel, the hub including a catch slidably engageable with the elongate member via said smooth surface; and
an annular latch member disposed within the outer barrel and engageable with the hub to inhibit rotation thereof, the annular latch member including a catch engageable with the first serrated channel, the first serrated channel being configured to enable movement of the latch member towards the first end of the outer barrel and inhibit movement of the latch member towards the second end of the outer barrel, the latch member including a rotation-locking recess, with at least a portion of the catch of the hub being shaped to extend within the rotation-locking recess of the latch member and the rotation-locking recess of the latch member inhibiting angular rotation of the hub thereby;
whereby during an injection the inner barrel, the hub and the latch member retract towards the first end of the outer barrel to enable the needle to enter into a patient's body, and thereafter the latch member is held in place via the catch thereof, while the hub and the inner barrel are resiliently biased outwards once more towards the second end of the outer barrel, with the catch of the hub dislodging from the rotation-locking recess of the latch member, at which point the guide member of the inner barrel promotes angular rotation of the catch of the hub from said smooth surface to the second serrated channel, which functions to inhibit further retraction of the inner barrel towards the first end of the outer barrel thereafter.

* * * * *

UNITED STATES PATENT AND TRADEMARK OFFICE
CERTIFICATE OF CORRECTION

PATENT NO. : 11,213,631 B2
APPLICATION NO. : 16/006732
DATED : January 4, 2022
INVENTOR(S) : Kim It is certified that error appears in the above-identified patent and that said Letters Patent is hereby corrected as shown below:

In the Claims

Column 15, Lines 31-47 should read:
1. A protected needle assembly having a longitudinal axis and comprising: a longitudinally-extending outer barrel receiving a needle therethrough; a longitudinally-extending inner barrel resiliently biased to extend about the needle in a protected needle mode; and a catch and serrate channel system configured to enable the inner barrel to at least partially retract into the outer barrel to deploy the needle for a one-time use, with subsequent retraction of the inner barrel being inhibited, wherein the catch and serrated channel system includes one or more channels which are longitudinally-extending, with the one or more channels including a continuous plurality of laterally-extending serrate edge portions therewithin.

Column 16, Lines 46-67 should read:
10. The assembly as claimed in claim 9 wherein one of the inner barrel and the hub includes at least one beveled surface shaped to promote rotation of the hub to the post-injection position.

11. The assembly as claimed in claim 9 further including a centrally-positioned elongate member, the elongate member including at least one channel through which the hub slidably engages with the outer barrel in the injection position, and the elongate member including at least one longitudinally-extending serrated edge portion which is circumferentially spaced from the channel and via which the hub engages in the post-injection position.

12. The assembly as claimed in claim 8 wherein the outer barrel has an interior, wherein the outer barrel includes at least one channel positioned within said interior, the channel of the outer barrel extending from adjacent the first end of the outer barrel towards the second end of the outer barrel, and wherein the inner barrel includes at least one radially outwardly-extending protrusion shaped to slidably engage with the channel of the outer barrel.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

Column 17, Lines 1-10 should read:

13. The assembly as claimed in claim 9 wherein the inner barrel includes at least one guide member that is angled at least in part, the guide member being shaped to promote angular rotation of the hub from the injection position to the post-injection position.

14. The assembly as claimed in claim 9 wherein the inner barrel includes at least one recess shaped to receive a portion of the hub when the hub is in the post-injection position and wherein the hub is rotatable to the post-injection position via a spring force.